United States Patent
He et al.

(10) Patent No.: US 11,191,724 B2
(45) Date of Patent: Dec. 7, 2021

(54) BRANCHED PEPTIDES FOR ENZYMATIC ASSEMBLY AND MITOCHONDRIA DRUG DELIVERY

(71) Applicant: BRANDEIS UNIVERSITY, Waltham, MA (US)

(72) Inventors: Hongjian He, Waltham, MA (US); Bing Xu, Newton, MA (US)

(73) Assignee: BRANDEIS UNIVERSITY, Waltham, MA (US)

( * ) Notice: Subject to any disclaimer, the term of this patent is extended or adjusted under 35 U.S.C. 154(b) by 0 days.

(21) Appl. No.: 16/648,295

(22) PCT Filed: Sep. 18, 2018

(86) PCT No.: PCT/US2018/051521
§ 371 (c)(1),
(2) Date: Mar. 18, 2020

(87) PCT Pub. No.: WO2019/055988
PCT Pub. Date: Mar. 21, 2019

(65) Prior Publication Data
US 2020/0281854 A1  Sep. 10, 2020

Related U.S. Application Data

(60) Provisional application No. 62/560,094, filed on Sep. 18, 2017.

(51) Int. Cl.
| | | |
|---|---|---|
| C07K 7/06 | (2006.01) |
| A61K 9/107 | (2006.01) |
| A61K 47/69 | (2017.01) |
| A61P 35/00 | (2006.01) |
| A61K 31/704 | (2006.01) |
| A61K 47/42 | (2017.01) |

(52) U.S. Cl.
CPC .......... *A61K 9/1075* (2013.01); *A61K 31/704* (2013.01); *A61K 47/42* (2013.01); *A61K 47/6907* (2017.08); *A61P 35/00* (2018.01); *C07K 7/06* (2013.01)

(58) Field of Classification Search
None
See application file for complete search history.

(56) References Cited

U.S. PATENT DOCUMENTS

| | | |
|---|---|---|
| 6,906,176 B2 | 6/2005 | Ley et al. |
| 2006/0165714 A1 | 7/2006 | Kern et al. |
| 2008/0268015 A1 | 10/2008 | Gron et al. |
| 2012/0142616 A1 | 6/2012 | Gao et al. |
| 2014/0148410 A1 | 5/2014 | Xu |
| 2014/0235550 A1 | 8/2014 | Gao et al. |
| 2016/0016994 A1 | 1/2016 | Xu et al. |
| 2017/0007696 A1 | 1/2017 | Zhao et al. |
| 2017/0037082 A1 | 2/2017 | Xu et al. |
| 2017/0119910 A1 | 5/2017 | Du et al. |
| 2018/0037605 A1 | 2/2018 | Du et al. |
| 2018/0346630 A1 | 12/2018 | Zhang et al. |
| 2019/0224330 A1 | 7/2019 | Wang et al. |
| 2020/0023065 A1 | 1/2020 | Xu |

FOREIGN PATENT DOCUMENTS

| | | |
|---|---|---|
| WO | 2010/151644 A2 | 12/2010 |
| WO | 2011/022056 A2 | 2/2011 |
| WO | 2012/166705 A2 | 12/2012 |
| WO | 2012/166706 A2 | 12/2012 |
| WO | 2014/074789 A1 | 5/2014 |
| WO | 2014/138367 A1 | 9/2014 |
| WO | 2015/116242 A1 | 8/2015 |
| WO | 2015/157530 A2 | 10/2015 |
| WO | 2015/157535 A2 | 10/2015 |
| WO | 2016/138433 A1 | 9/2016 |
| WO | 2017/189996 A1 | 11/2017 |
| WO | 2018/129171 A1 | 7/2018 |
| WO | 2019/035928 A1 | 2/2019 |

OTHER PUBLICATIONS

He et al., "Branched Peptides for Enzymatic Supramolecular Hydrogelation," Chem. Commun. 54:86-89 (2018).
Kim, et al., "Substrate Specificities of Porcine and Bovine Enteropeptidases towards the Peptide Val-(Asp)4-Lys-Ile-Val-Gly and Its Analogs," Biosci. Biotechnol. Biochem. 72(3):905-908 (2008).
Waugh, D., "An Overview of Enzymatic Reagents for the Removal of Affinity Tags," Protein Expres. Purif. 80(2): 283-293 (2011).
Nguyen et al., "Modulation of the Protein Kinase Cdelta Interaction with the "d" Subunit of F1F0-ATP Synthase in Neonatal Cardiac Myocytes: Development of Cell-Permeable, Mitochondrially Targeted Inhibitor and Facilitator Peptides," J. Biol. Chem. 285(29):22164-22173 (2010).
International Search Report and Written Opinion for corresponding PCT Application No. PCT/US2018/051521, dated Jan. 18, 2019.
Mel et al., "Enzyme-instructed Self-Assembly of Taxol Promotes Axonal Branching," Nanoscale 7(38):15605-15608 (2015).

*Primary Examiner* — Thomas S Heard
(74) *Attorney, Agent, or Firm* — Troutman Pepper Hamilton Sanders LLP (Rochester)

(57) ABSTRACT

The present invention relates to a branched peptide that includes a first peptide chain and a second peptide chain having its C-terminal amino acid covalently linked to a sidechain of an amino acid residue of the first peptide chain, wherein the first peptide chain includes a plurality of aromatic amino acids and, optionally, an aromatic group linked to an amino terminus of the first peptide chain; and the second peptide chain includes a plurality of hydrophilic amino acids and an enzyme cleavage site. Pharmaceutical compositions containing the branched peptide and one or more therapeutic agents in an aqueous medium are disclosed, where the branched peptides form micelle structures in the aqueous medium. Methods of using the pharmaceutical composition to deliver therapeutic agents, and for treating various disease conditions are also described.

19 Claims, 13 Drawing Sheets
Specification includes a Sequence Listing.

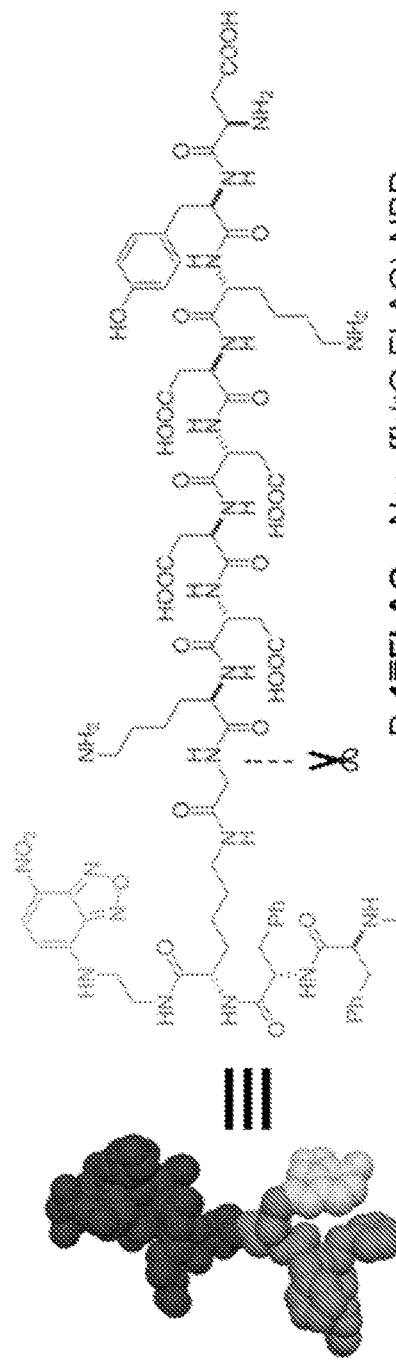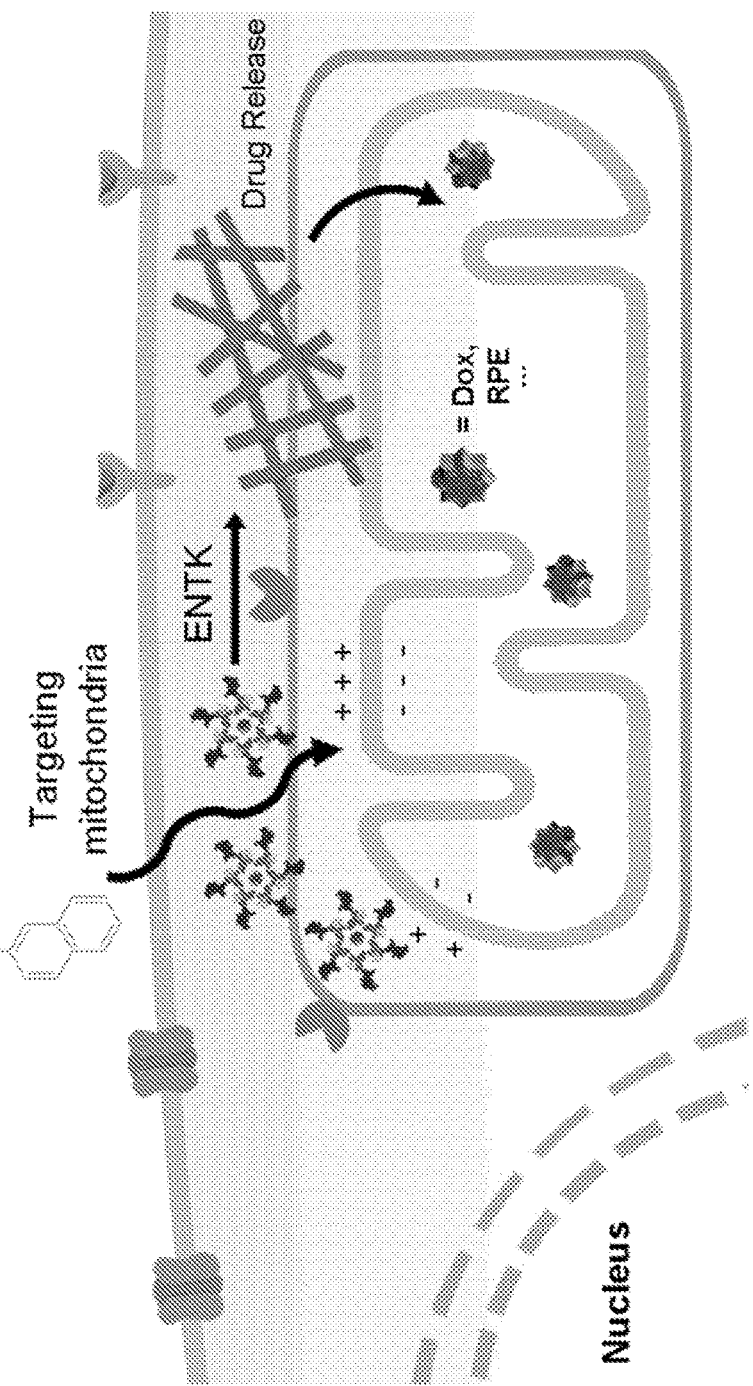
FIG. 1

FIGS. 5A-D

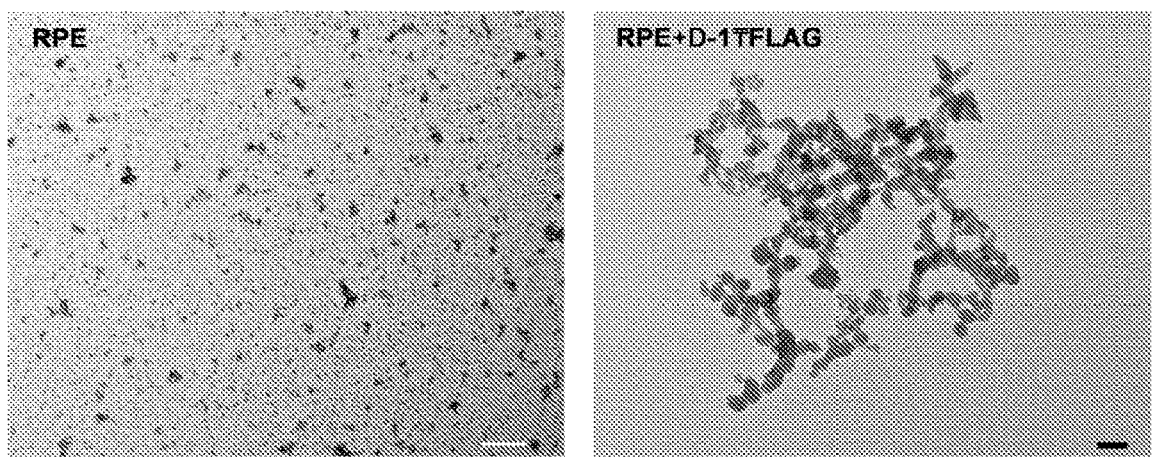
*FIG. 6*
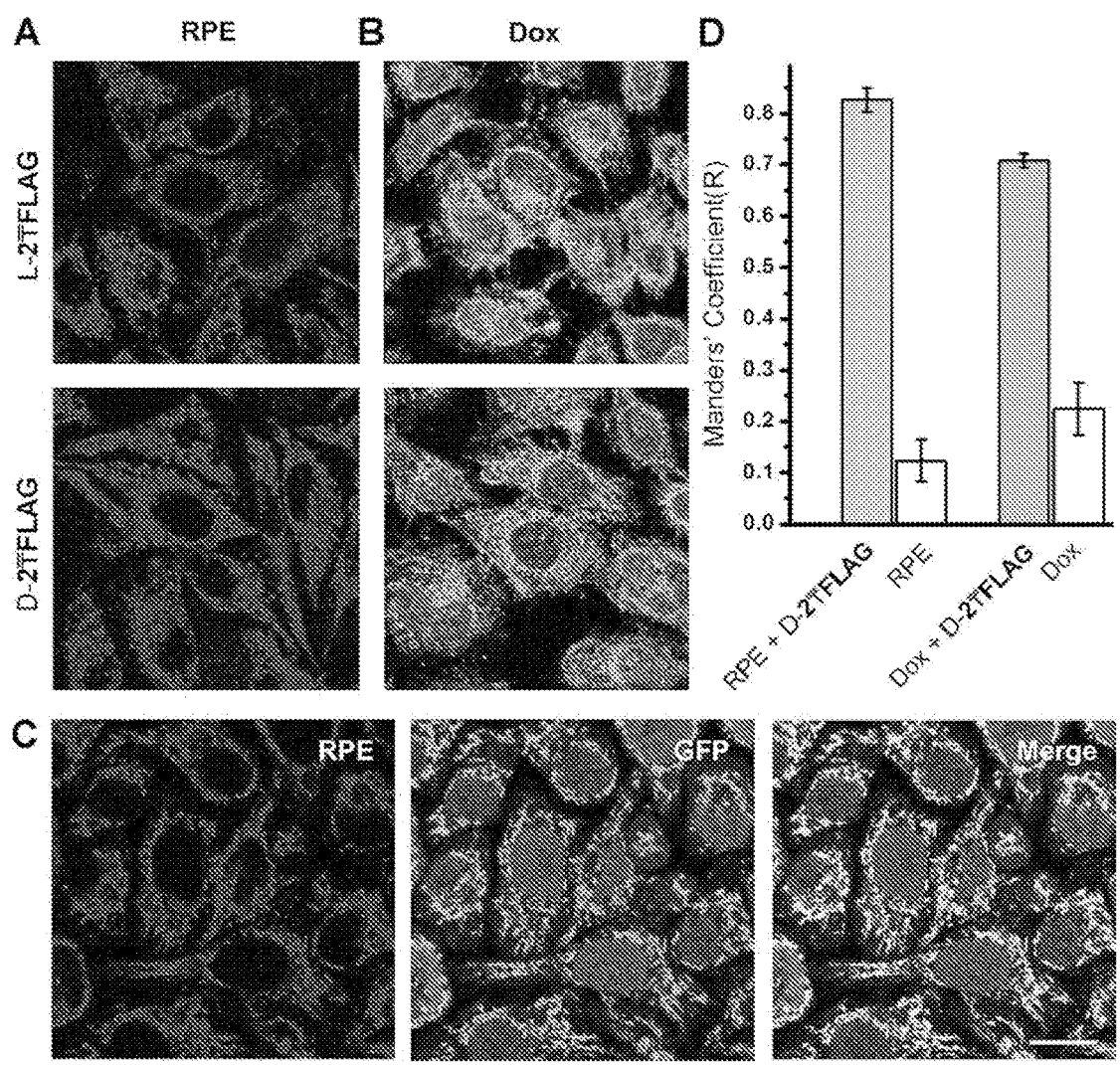
*FIGS. 7A-D*

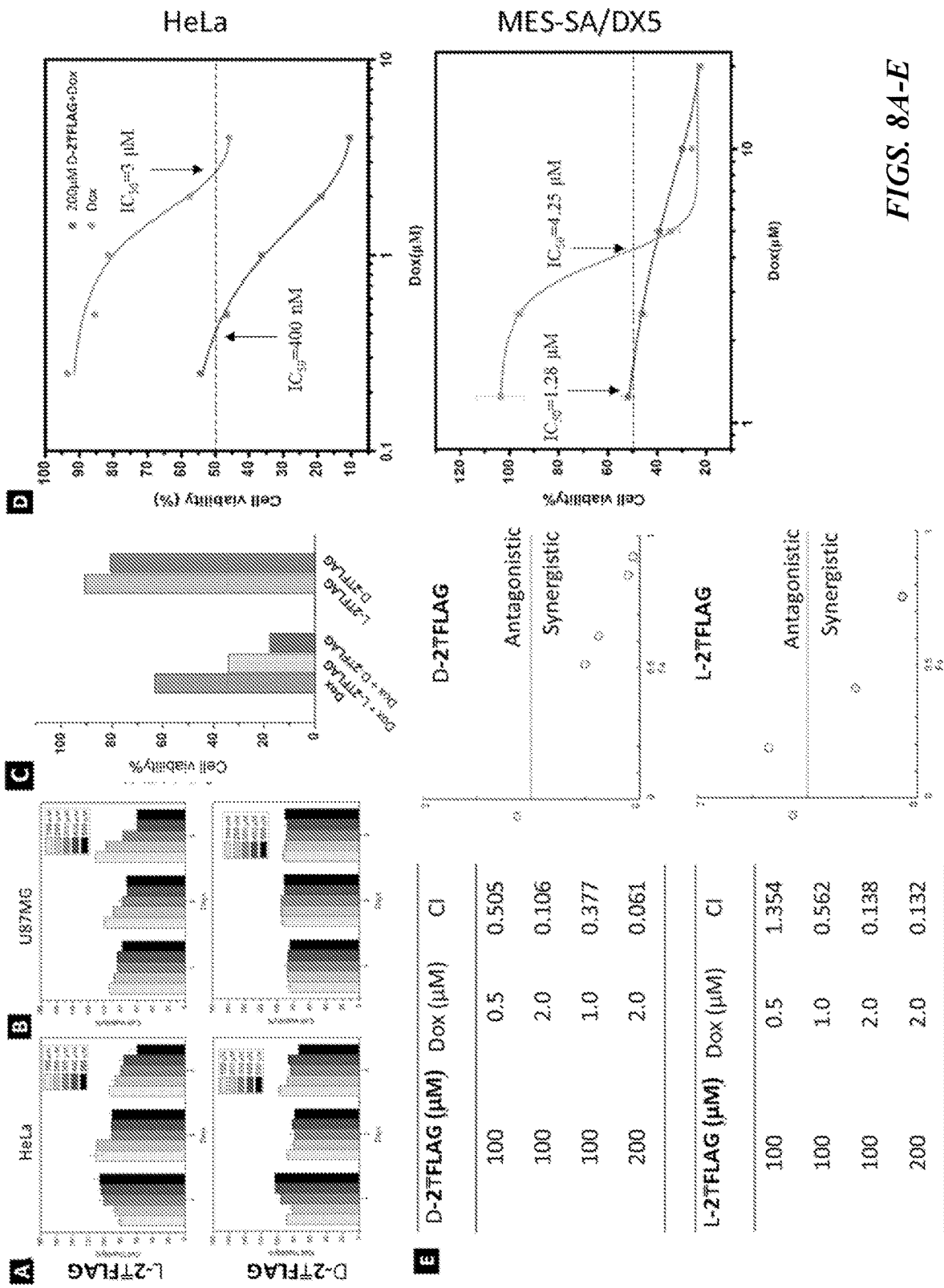
FIGS. 8A-E

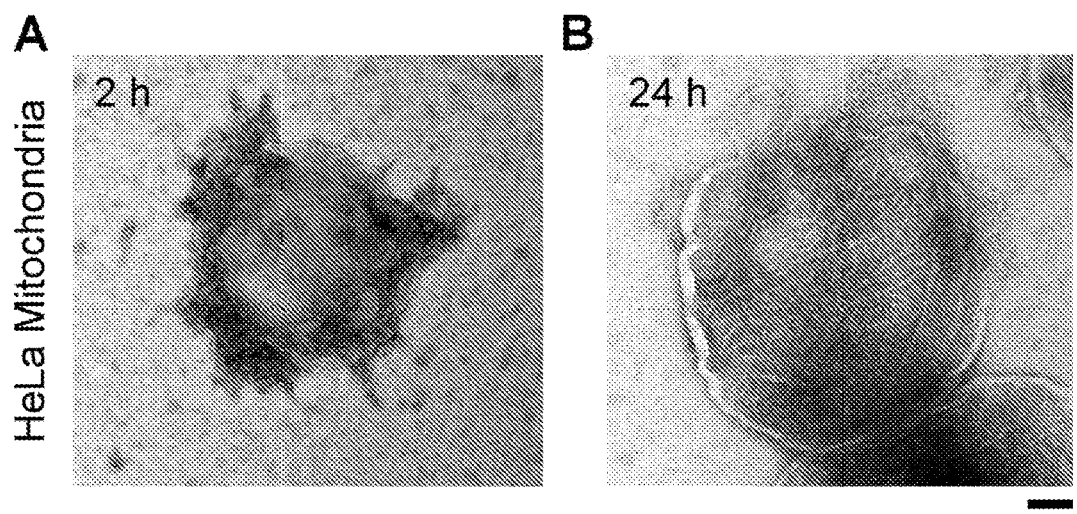
*FIGS. 9A-B*
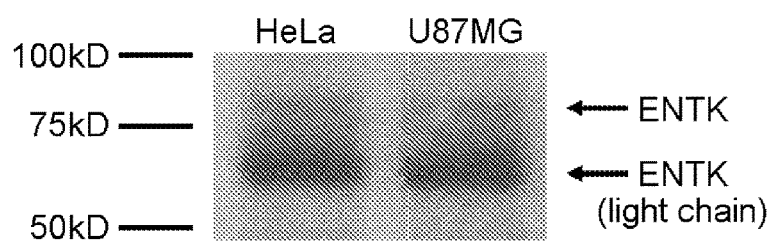
*FIG. 10*
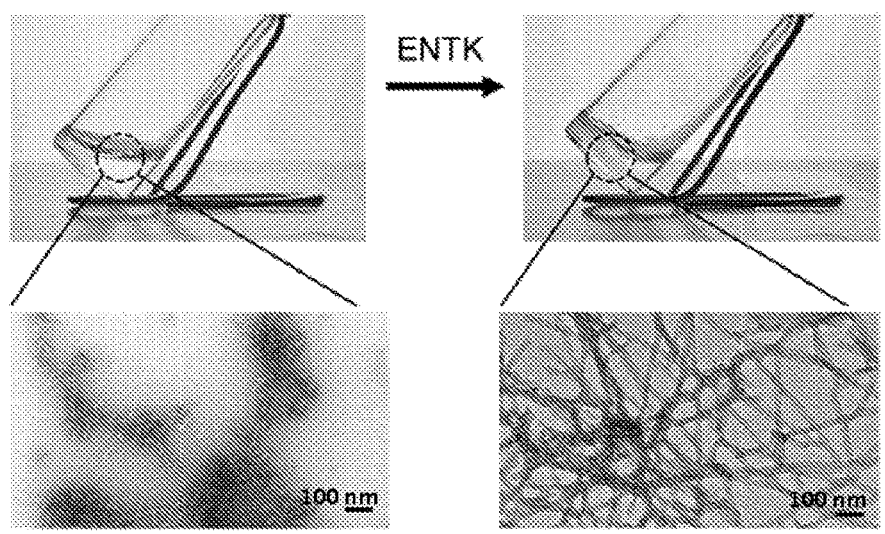
*FIG. 11*

BRANCHED PEPTIDES FOR ENZYMATIC ASSEMBLY AND MITOCHONDRIA DRUG DELIVERY

This application is a national stage application under 35 U.S.C. § 371 of PCT Application No. PCT/US2018/051521, filed Sep. 18, 2018, which claims the benefit of U.S. Provisional Patent Application Ser. No. 62/560,094, filed Sep. 18, 2017, which is hereby incorporated by reference in its entirety.

This invention was made with government support under grant CA142746 awarded by the National Institutes of Health and grant MRSEC-1420382 awarded by the National Science Foundation. The government has certain rights in the invention.

FIELD OF THE INVENTION

The present invention relates to branched peptides capable of forming micelles when introduced to aqueous medium, enzymatically induced self-assembly of the cleaved peptide products, pharmaceutical compositions containing the branched peptides, and their use to deliver cargo to the mitochondria of cells.

BACKGROUND OF THE INVENTION

As a subcellular organelle, mitochondria play essential roles in many cellular processes, such as apoptosis and metabolism (Green et al., *Science* 305(5684):626-629 (2004); McBride et al., *Curr. Biol.* 16(14):R551-R560 (2006); Kujoth et al., *Science* 309(5733):481-484 (2005); Balaban et al., *Cell* 120(4):483-495 (2005)). Intensive research efforts have focused on developing therapeutics that target mitochondria (Hoye et al., *Acc. Chem. Res.* 41(1):87-97 (2008); Murphy et al., *Annual Review of Pharmacology and Toxicology* 47:629-656 (2007); Yousif et al., *Chembiochem* 10(12):1939-1950 (2009)). In fact, some of the therapeutics have already entered clinical trials (Thomas et al., *J. Am. Soc. Nephrol.* 18(1):213-222 (2007); Birk et al., *J. Am. Soc. Nephrol.* 24(8):1250-1261 (2013); Trachootham et al., *Nat. Rev. Drug. Discov.* 8(7):579-591 (2009)). With the exception of gramicidin S derivatives developed by Wipf et al. (Hoye et al., *Acc. Chem. Res.* 41(1):87-97 (2008)), most of the molecules reported for targeting mitochondria are lipophilic and cationic (Yousif et al., *Chembiochem* 10(12):2081-2088 (2009); Mahon et al., *Chem. & Bio.* 14(8):923-930 (2007); Zhao et al., *Biochem. Pharmacol.* 70(12):1796-1806 (2005); Smith et al., *Eur. J. Biochem.* 263(3):709-716 (1999); Murphy et al., *Annu. Rev. Pharmacol. Toxicol.* 47:629-656 (2007); Murphy, M. P., *Trends Biotechnol.* 15(8):326-330 (1997); Hurt et al., *EMBO J.* 4(13A):3509-3518 (1985); Horton et al., *Chem. Biol.* 15(4): 375-382 (2008); Hoye et al., *Acc. Chem. Res.* 41(1):87-97 (2008)). Although those lipophilic cations are able to prevent mitochondrial damage in vitro, they have a major drawback due the toxicity that results from the accumulation in the mitochondrial matrix (Murphy, M. P., *Trends Biotechnol.* 15(8):326-330 (1997)). Thus, it is both desirable and necessary to develop new molecules and processes for targeting mitochondria.

The present invention is directed to overcoming these and other deficiencies in the art.

SUMMARY OF THE INVENTION

A first aspect of the invention relates to a branched peptide that includes a first peptide chain and a second peptide chain having its C-terminal amino acid covalently linked to a sidechain of an amino acid residue of the first peptide chain. The first peptide chain includes a plurality of aromatic amino acids and, optionally, an aromatic group linked to an amino terminus of the first peptide chain. The second peptide chain comprises a plurality of hydrophilic amino acids and an enzyme cleavage site.

A second aspect of the invention relates to a pharmaceutical composition comprising the branched peptide according to the first aspect of the invention in an aqueous medium. The pharmaceutical composition may include one or more therapeutic agents in combination with the branched peptides. In accordance with this aspect of the invention, the branched peptides form micelle structures in the aqueous medium.

A third aspect of the invention relates to a method of delivering a therapeutic agent into mitochondria comprising encapsulating a therapeutic agent within a micelle structure of the pharmaceutical composition according to the second aspect of the invention. A cell is contacted with the pharmaceutical composition, whereby micelle structures are taken up by the cell and targeted to mitochondria within the cell. As a consequence of the micelle structures being targeted to the mitochondria, the therapeutic agent is thereby delivered to the mitochondria.

A fourth aspect of the invention relates to a nanofiber formed in an aqueous medium comprising a self-assembled, enzymatically modified form of the branched peptide of the first aspect of the invention.

A fifth aspect of the invention relates to a supramolecular hydrogel formed in an aqueous medium and comprising a self-assembled, enzymatically modified form of the branched peptide of the first aspect of the invention.

A sixth aspect of the invention relates to a method of treating a patient having a cancerous condition comprising: administering a pharmaceutical composition according the second aspect of the invention to a patient having a cancerous condition, where the administering is effective to inhibit cancer cell survival. In this aspect of the invention, the pharmaceutical composition also includes a therapeutic agent effective for treating cancer cells, i.e., inhibiting cancer cell survival.

A seventh aspect of the invention relates to a method of treating an individual exposed to radiation comprising: administering a pharmaceutical composition according to the second aspect of the invention to an individual exposed to, or about to be exposed to radiation, where the administering is effective to inhibit radiation-induced damage to cells of the individual. In this aspect of the invention, the pharmaceutical composition also includes a therapeutic (or prophylactic) agent effective to inhibit radiation-induced damage to cells.

An eighth aspect of the invention relates to a method of treating a patient for a cardiovascular disease or condition, the method comprising: administering a pharmaceutical composition according to the second aspect of the invention, to an individual having a cardiovascular disease or condition, where the administering is effective to inhibit radiation-induced damage to cells of the individual. In this aspect of the invention, the pharmaceutical composition also includes a therapeutic agent effective for treating a cardiovascular disease or condition.

In any of the preceding aspects, the peptide can be conjugated to a therapeutic agent, or a therapeutic agent in non-conjugated form can be present in the products, hydrogels, or pharmaceutical compositions of the invention, such that the therapeutic agent is captured or retained in any hydrogel product formed thereby.

The accompanying Examples demonstrate the enzymatic cleavage of branched peptides that carry negative charges for targeting mitochondria. Conjugating a well-established protein tag, i.e., FLAG-tag (Hopp et al., *Nat. Biotechnol.* 6(10):1204-1210 (1988), which is hereby incorporated by reference in its entirety) to self-assembling motifs (Reches & Gazit, *Science* 300(5619):625-627 (2003); Burattini et al., *J. Am. Chem. Soc.* 132(34):12051-12058 (2010); Zhang et al., *Langmuir* 27(2):529-537 (2010), which are hereby incorporated by reference in their entirety) affords the precursors that are the substrates of enterokinase (ENTK) (Pavlov & Thompson, *The Work of the Digestive Glands*, London: Charles Griffin & Company, Limited (1902), which is hereby incorporated by reference in its entirety). The precursors form micelles, which upon enzymatic cleavage of the hydrophilic branch that contains the FLAG motif (DDDDK) (Hopp et al., *Nat. Biotechnol.* 6(10):1204-1210 (1988), which is hereby incorporated by reference in its entirety) turn into nanofibers. Fluorescent microscopy of live cells reveals that, after being taken up by cells, the branched peptides and their enzyme cleaved products, mainly localize to the mitochondria. Moreover, the micelles of the precursors are able to deliver cargo, including small molecules (as exemplified by doxorubicin (Dox)), viral vectors (as exemplified by baculovirus), and proteins (as exemplified by red phycoerythrin (RPE)(Teale & Dale, *Biochem. J.* 116(2):161-169 (1970), which is hereby incorporated by reference in its entirety) into cells, largely to mitochondria and within about two hours. Western blot indicates ENTK on the isolated mitochondria of cancer cells, and transmission electron microscopy (TEM) of the isolated mitochondria confirms the conversion of the micelles to nanofibers at the mitochondria. Preventing ENTK proteolysis diminishes the mitochondria targeting. These results confirm EISA as the process for targeting mitochondria. As the first report of using EISA for targeting mitochondria and delivery of molecular cargo to mitochondria (see FIG. 1), this application and its accompanying Examples illustrate a fundamentally new molecular motif and process for targeting mitochondria and exploring the applications of protease-instructed assembly for biomedicine.

BRIEF DESCRIPTION OF THE DRAWINGS

FIG. 1 is a schematic illustration of the structure of a representative branched peptide, its cellular uptake and ENTK-induced cleavage of the branched peptide to convert micelles into nanofibers assembled on mitochondria.

FIG. 5A are TEM images of D-1⊤FLAG before (left) and after (right) adding ENTK (24 h), scale bar=100 nm. FIG. 5B are fluorescent images of HeLa and U87MG cells incubated with D-1⊤FLAG for 2 h. FIG. 5C are fluorescence images of D-1⊤FLAG and MitoTracker in HeLa cells. FIG. 5D are HeLa cells treated by the mixture of RPE (1 µg/mL) and D-1⊤FLAG for 2 h. Scale bar=30 µm in (B, C). The concentration of D-1⊤FLAG is 200 µM for A-D.

FIG. 6 is a pair of TEM image of RPE and the mixture of RPE and D-1⊤FLAG. The clear background in the TEM image of the mixture indicates the encapsulation of RPE by D-1⊤FLAG. Scale bar=100 nm.

FIGS. 7A-D display the difference between D-2⊤FLAG and L-2⊤FLAG. In FIGS. 7A-B, HeLa cells incubated separately with RPE (1 µg/mL) and Dox (2 µM) while mixing with D-2⊤FLAG and L-2⊤FLAG (200 µM) for 2 h. In FIG. 7C, GFP-cyt c HeLa cells were treated by the mixture of RPE (1 µg/ml) and D-2⊤FLAG (200 µM) for 2 h. Scale bar=30 FIG. 7D is a graph showing the co-localization analysis of GFP-cyt c and Omi-mcherry expressing HeLa cells treated by RPE or Dox in the presence of D-2⊤FLAG. R=1 indicates perfect co-localization.

FIGS. 8A-E display the cytotoxicity data of D-2⊤FLAG. FIGS. 8A-B are graphical representations of the cytotoxicity data of L-2⊤FLAG and D-2⊤FLAG against HeLa and U87MG cells, respectively. FIGS. 8C-D show the combination of Dox (2 µM) and L-2⊤FLAG and D-2⊤FLAG exhibit increased cancer cell inhibition. FIG. 8E shows the synergistic effect on the inhibition of cancer cells are gained by Compusyn (Chou, *Pharmacol. Rev.* 58(3):621(2006), which is hereby incorporated by reference in its entirety). CI<1 means synergistic effect, >1 means antagonistic effect, =1 means additive effect.

FIGS. 9A-B are TEM images of mitochondria isolated from HeLa cells being incubated with D-2⊤FLAG (200 µM) for 2 h (FIG. 9A) and 24 h (FIG. 9B). Scale bar equals 100 nm.

FIG. 10 show the western blot analysis of ENTK in the mitochondria lisolated from HeLa and U87MG cells. The present of ENTK light chain may due to the fact that the disulfide bond linking the light chain and heavy chain of ENTK was broken (reduced) by 2-mercaptoethanol (Anfinsen et al., *J. Biol. Chem.* 236(5):1361(1961), which is hereby incorporated by reference in its entirety) included in the loading buffer for western blot experiments.

FIG. 11 are images of the Sol/micelles-gel/fibers transition of Mito-Flag (also referred to as D-2⊤FLAG) by ENTK in solution. The concentration of Mito-Flag for producing hydrogel is 2.5 wt %. For TEM images, the concentration of Mito-Flag is 200 µM. ENTK concentration is 10 U/ml for all samples. The incubation time is 24 h.

DETAILED DESCRIPTION OF THE INVENTION

Figure 2:
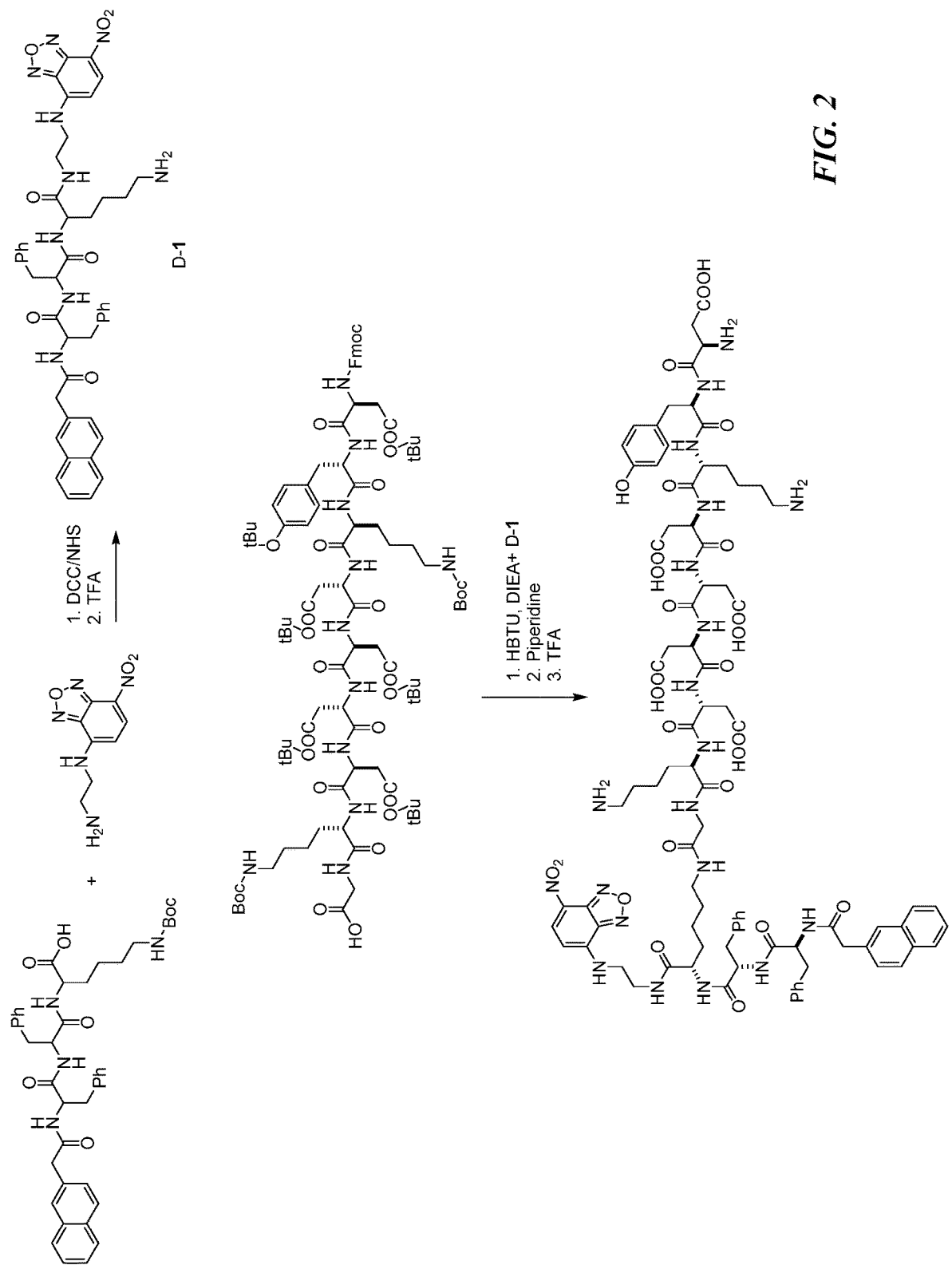
FIG. 2 is an exemplary synthetic route for the formation of branched peptides, and illustrated the structure of D-1, which includes the fluorophore NBD, and its use in the synthesis of D-1⊤FLAG.

One aspect of the invention relates to a branched peptide that includes a first peptide chain and a second peptide chain having its C-terminal amino acid covalently linked to a sidechain of an amino acid residue of the first peptide chain. The first peptide chain includes a plurality of aromatic amino acids and, optionally, an aromatic group linked to an amino terminus of the first peptide chain. The second peptide chain comprises a plurality of hydrophilic amino acids and an enzyme cleavage site. As discussed more fully below, the branched peptides are capable of forming micelle structures in an aqueous medium and, following enzymatic cleavage of the second peptide chain at the enzyme cleavage site, the resulting (branched) peptide is capable of self-assembling to form nanofibers and, eventually, a hydrogel in an aqueous medium.

The term "amino acid" further includes analogues, derivatives, and congeners of any specific amino acid referred to herein, as well as C-terminal or N-terminal protected amino acid derivatives (e.g., modified with an N-terminal or C-terminal protecting group). Furthermore, the term "amino acid" includes both D- and L-amino acids. Hence, an amino acid which is identified herein by its name, three letter or one letter symbol and is not identified specifically as having the D or L configuration, is understood to assume any one of the D or L configurations. For example, 2-Nal or 2-Nal$_D$ refer to the L and D configurations, respectively, of the analogue 3-(2-naphthyl)-alanine.

Naturally occurring amino acids are identified throughout by the conventional three-letter and/or one-letter abbreviations, corresponding to the trivial name of the amino acid, in accordance with the following list: Alanine (Ala), Arginine (Arg), Asparagine (Asn), Aspartic acid (Asp), Cysteine (Cys), Glutamic acid (Glu), Glutamine (Gln), Glycine (Gly), Histidine (His), Isoleucine (Ile), Leucine (Leu), Lysine (Lys), Methionine (Met), Phenylalanine (Phe), Proline (Pro), Serine (Ser), Threonine (Thr), Tryptophan (Trp), Tyrosine (Tyr), and Valine (Val). The abbreviations are accepted in the peptide art and are recommended by the IUPAC-IUB commission in biochemical nomenclature As used herein the term "peptide" includes native peptides (either degradation products or synthetically synthesized peptides) and further to peptidomimetics, such as peptoids and semipeptoids which are peptide analogs, which may have, for example, modifications rendering the peptides more stable while in a body, having lower immunogenicity and/or higher affinity to their receptors.

As used herein, the term "about" when used in connection with a numerical value denotes an interval of accuracy that is ±10% in certain embodiments, ±5% in other embodiments, ±2.5% in still further embodiments, and ±1% in yet another embodiment.

As used herein and in the appended claims, the singular "a", "an" and "the" include the plural reference unless the context clearly dictates otherwise. Thus, for example, reference to a "peptide" includes a plurality of such peptides.

In some embodiments of the invention, the branched peptide, following enzymatic cleavage of the second peptide chain at the enzyme cleavage site, is capable of self-assembling to form nanofibers containing the cleavage product and a hydrogel composed of such nanofibers, when present in an aqueous medium. A hydrogel may be defined as a three-dimensional, hydrophilic or amphiphilic polymeric network capable of taking up a quantity of water, typically a large quantity of water. The networks are composed of homopolymers or copolymers, are insoluble due to the presence of covalent chemical or physical (ionic, hydrophobic interactions, entanglements) crosslinks. The crosslinks provide the network structure and physical integrity. Hydrogels exhibit a thermodynamic compatibility with water that allows them to swell in aqueous media. The chains of the network are connected in such a fashion that pores exist and that a substantial fraction of these pores are of dimensions between 1 nm and 1000 nm.

As used herein and is well-known in the art, the term "hydrogel" refers to a material that comprises fibrous networks formed of water-soluble natural or synthetic polymer chains, typically (though not exclusively) containing more than 95% water, often more than 96%, 97%, 98%, or 99% water.

The term "gelling" or "gelation" means a thickening of the medium that may result in a gelatinous consistency and even in a solid, rigid consistency that does not flow under its own weight.

A "gelator" is defined herein to include a non-polymeric organic compound whose molecules can establish, between themselves, at least one physical interaction leading to a self-assembly of the molecules in a carrier fluid to form a gel. The gel may result from the formation of a network of molecular nanofibers due to the stacking or aggregation of gelator molecules. The gelator is the product of enzymatic cleavage of the branched peptide.

The first peptide chain can have any length that is sufficient to allow for self-assembly after enzymatic cleavage (of the second peptide chain of the branched peptide). This includes peptides up to about 70 amino acids, up to about 65 amino acids, up to about 60 amino acids, up to about 55 amino acids, up to about 50 amino acids, up to about 45 amino acids, up to about 40 amino acids, up to about 35 amino acids, up to about 30 amino acids, up to about 25 amino acids, up to about 20 amino acids, up to about 15 amino acids, or up to about 10 amino acids. In certain embodiments, the first peptide chain is less than 20 amino acids in length.

In certain embodiments of the invention, the first peptide chain contains only D-amino acids. In an alternative embodiment, the first peptide chain contains only L-amino acids, or a mixture of L- and D-amino acids.

To promote self-assembly, the first peptide chain preferably includes aromatic amino acids, including one or more of phenylalanine, tyrosine, and tryptophan, or any derivatives thereof.

In the first peptide chain, the amino acid residue to which the second peptide chain is covalently linked is one that has (or had, prior to such covalent linkage) a reactive sidechain. This amino acid having the reactive sidechain can be (i) one having a basic sidechain with a reactive amino group, such as Arg or Lys; or (ii) one having a nucleophilic sidechain with a reactive hydroxyl group or thiol group, such as Ser or Thr or Cys, but preferably Ser or Cys; or (iii) one having a basic sidechain with a reactive imidazole group, such as His. The amino acids having a reactive amino group will form a —NH—C(O)— covalent bond with the second peptide C-terminus as described in the accompanying Examples. The amino acids having a reactive hydroxyl group will form a —O—C(O)— covalent bond with the second peptide C-terminus (see Ono et al., *Bull. Chem. Soc. Japan* 51(8): 2401-2404 (1978), which is hereby incorporated by reference in its entirety). The amino acids having a reactive thiol group will form a —S—C(O)— covalent bond with the second peptide C-terminus (see Ingenito et al., JACS 121: 11369-74 (1999), which is hereby incorporated by reference in its entirety).

In one embodiment, the first peptide chain includes an aromatic group linked to the amino terminus of the first peptide chain. The aromatic group can be any suitable single- or multi-ring aromatic moiety that facilitates self-assembly as discussed herein. Exemplary aromatic groups include, without limitation, phenylacetyl, naphthylacetyl, fluorenylacetyl, pyrenylacetyl, and cinnamoyl.

Exemplary first peptide chains of the present invention include, without limitation: napthylacetyl-FFKY (SEQ ID NO: 1), napthylacetyl-FFFKY (SEQ ID NO: 2), napthylacetyl-FFGKY (SEQ ID NO: 3), napthylacetyl-FFGK (SEQ ID NO: 4), napthylacetyl-FFGKF (SEQ ID NO: 5), napthylacetyl-ffky, napthylacetyl-fffky, napthylacetyl-ffgky, napthylacetyl-ffgk, napthylacetyl-ffgkf, napthylacetyl-FFK(Dmt) (SEQ ID NO: 6), napthylacetyl-FFFK(Dmt) (SEQ ID NO: 7), napthylacetyl-FFGK(Dmt) (SEQ ID NO: 8), napthylacetyl-ffk(dmt), napthylacetyl-fffk(dmt), napthylacetyl-ffgk(dmt), napthylacetyl-FFCY (SEQ ID NO: 9), napthylacetyl-FFFCY (SEQ ID NO: 10), napthylacetyl-FFGCY (SEQ ID NO: 11), napthylacetyl-FFGC (SEQ ID NO: 12), napthylacetyl-FFGCF (SEQ ID NO: 13), napthylacetyl-ffcy, napthylacetyl-fffcy, napthylacetyl-ffgcy, napthylacetyl-ffgc, napthylacetyl-ffgcf, napthylacetyl-FFC(Dmt) (SEQ ID NO: 14), napthylacetyl-FFFC(Dmt) (SEQ ID NO: 15), napthylacetyl-FFGC(Dmt) (SEQ ID NO: 16), napthylacetyl-ffc(dmt), napthylacetyl-fffc(dmt), napthylacetyl-ffgc(dmt), where Dmt is 2,6-dimethyl-L-tyrosine and dmt is 2,6-dimethyl-D-tyrosine, and where the second peptide chain is linked to the sidechain of the lysine or cysteine residue.

In certain embodiments, the first peptide chain further includes a therapeutic agent, Z, covalently bonded to the C-terminal residue of first peptide chain. Covalent attachment may be carried out directly to the C-terminus or following amidation of the C-terminus. By way of example only, one such first peptide is napthylacetyl-FFKY-Z (SEQ ID NO: 1), where the tyrosine moiety is covalently linked to the therapeutic agent. The therapeutic agent, Z, can be any type of therapeutic agent that is capable of being so-modified. Exemplary therapeutic agents include, without limitation, antioxidants, coenzymes, vitamins, metabolites, analgesics, anti-inflammatory agents, antihelminthics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-thrombogenic agents, anti-claudication agents, anti-atherosclerotic drugs, vascular agents, anti-malarials, anti-migraine agents, anti-muscarinic agents, anti-neoplastic agents, erectile dysfunction improvement agents, immuno-suppressants, anti-protozoal agents, anti-thyroid agents, anxiolytic agents, sedatives, hypnotics, neuroleptics, β-blockers, cardiac inotropic agents, corticosteroids, diuretics, anti-parkinsonian agents, gastro-intestinal agents, histamine receptor antagonists, keratolyptics, lipid regulating agents, anti-anginal agents, Cox-2 inhibitors, leukotriene inhibitors, macrolides, muscle relaxants, nutritional agents, opioid analgesics, protease inhibitors, sex hormones, stimulants, anti-osteoporosis agents, anti-obesity agents, cognition enhancers, anti-urinary incontinence agents, anti-benign prostate hypertrophy agents, essential fatty acids, non-essential fatty acids, cytokines, growth factors, antibodies, radioprotective agents, and cardioprotective agents.

In certain embodiments of the invention, the second peptide chain comprises not more than 50 amino acid residues between the enzyme cleavage site and the covalent bond formed between the first and second peptide chains. In a further embodiment, the second peptide chain comprises a single amino acid residue between the cleavage site and the covalent bond between the peptide chains, where the single amino acid is other than Trp or Pro.

The second peptide chain preferably comprises L-amino acids, which improves its susceptibility to enzymatic cleavage.

As noted above, the second peptide chain includes an enzyme cleavage site. While various enzyme cleavage sites are contemplated, preferred enzyme cleavage sites are those that are acted upon by endoenzymes that have specificity for a particular amino acid sequence. One preferred class of enzymes cleavage sites are enterokinase cleavage sites.

Exemplary amino acid sequences of the second peptide chain of the present invention include, without limitation: DDDDK (SEQ ID NO: 17), KDDDK (SEQ ID NO: 18), DDDDR (SEQ ID NO: 19), KDDDR (SEQ ID NO: 20), DADDK (SEQ ID NO: 21), KADDK (SEQ ID NO: 22), DADDR (SEQ ID NO: 23), KADDR (SEQ ID NO: 24), DEDDK (SEQ ID NO: 25), KEDDK (SEQ ID NO: 26), DEDDR (SEQ ID NO: 27), KEDDR (SEQ ID NO: 28), EDDDK (SEQ ID NO: 29), EDDDR (SEQ ID NO: 30), EEDDK (SEQ ID NO: 31), EEDDR (SEQ ID NO: 32), DLYDDDDK (SEQ ID NO: 33), DLYDDDDR (SEQ ID NO: 34), DYKDDDDK (SEQ ID NO: 35), DYKDDDDR (SEQ ID NO: 36), DYKDADDK (SEQ ID NO: 37), DYKDADDR (SEQ ID NO: 38), DYKDEDDK (SEQ ID NO: 39), DYKDEDDR (SEQ ID NO: 40), DYKEDDDK (SEQ ID NO: 41), DYKEDDDR (SEQ ID NO: 42), DYKEEDDK (SEQ ID NO: 43), DYKEEDDR (SEQ ID NO: 44), and LKGDR (SEQ ID NO: 45) (Shahravan et al., *Protein Expr. Purif.* 59(2):314-319 (2008), which is hereby incorporated by reference in its entirety). Variations of the above-identified peptides are also contemplated where additional amino acid residues are introduced between the cleavage site and the C-terminal residue, or where additional N-terminal amino acids are introduced to the second peptide chain.

Additional exemplary amino acid sequences of the second peptide chain of the present invention include, without limitation:

```
                                           (SEQ ID NO: 46)
DDDDK(G/A/T/S/Y/H/Q/E/N/D/R/K), (SEQ ID NO: 47)
KDDDK(G/A/T/S/Y/H/Q/E/N/D/R/K),
```

DDDDR(G/A/T/S/Y/H/Q/E/N/D/R/K), (SEQ ID NO: 48)

KDDDR(G/A/T/S/Y/H/Q/E/N/D/R/K), (SEQ ID NO: 49)

DADDK(G/A/T/S/Y/H/Q/E/N/D/R/K), (SEQ ID NO: 50)

KADDK(G/A/T/S/Y/H/Q/E/N/D/R/K), (SEQ ID NO: 51)

DADDR(G/A/T/S/Y/H/Q/E/N/D/R/K), (SEQ ID NO: 52)

KADDR(G/A/T/S/Y/H/Q/E/N/D/R/K), (SEQ ID NO: 53)

DEDDK(G/A/T/S/Y/H/Q/E/N/D/R/K), (SEQ ID NO: 54)

KEDDK(G/A/T/S/Y/H/Q/E/N/D/R/K), (SEQ ID NO: 55)

DEDDR(G/A/T/S/Y/H/Q/E/N/D/R/K), (SEQ ID NO: 56)

KEDDR(G/A/T/S/Y/H/Q/E/N/D/R/K), (SEQ ID NO: 57)

EDDDK(G/A/T/S/Y/H/Q/E/N/D/R/K), (SEQ ID NO: 58)

EDDDR(G/A/T/S/Y/H/Q/E/N/D/R/K), (SEQ ID NO: 59)

EEDDK(G/A/T/S/Y/H/Q/E/N/D/R/K), (SEQ ID NO: 60)

EEDDR(G/A/T/S/Y/H/Q/E/N/D/R/K), (SEQ ID NO: 61)

DLYDDDDK(G/A/T/S/Y/H/Q/E/N/D/R/K), (SEQ ID NO: 62)

DLYDDDDR(G/A/T/S/Y/H/Q/E/N/D/R/K), (SEQ ID NO: 63)

DYKDDDDK(G/A/T/S/Y/H/Q/E/N/D/R/K), (SEQ ID NO: 64)

DYKDDDDR(G/A/T/S/Y/H/Q/E/N/D/R/K), (SEQ ID NO: 65)

DYKDADDK(G/A/T/S/Y/H/Q/E/N/D/R/K), (SEQ ID NO: 66)

DYKDADDR(G/A/T/S/Y/H/Q/E/N/D/R/K), (SEQ ID NO: 67)

DYKDEDDK(G/A/T/S/Y/H/Q/E/N/D/R/K), (SEQ ID NO: 68)

DYKDEDDR(G/A/T/S/Y/H/Q/E/N/D/R/K), (SEQ ID NO: 69)

DYKEDDDK(G/A/T/S/Y/H/Q/E/N/D/R/K), (SEQ ID NO: 70)

DYKEDDDR(G/A/T/S/Y/H/Q/E/N/D/R/K), (SEQ ID NO: 71)

DYKEEDDK(G/A/T/S/Y/H/Q/E/N/D/R/K), (SEQ ID NO: 72)

DYKEEDDR(G/A/T/S/Y/H/Q/E/N/D/R/K), (SEQ ID NO: 73)
and

LKGDR(G/A/T/S/Y/H/Q/E/N/D/R/K). (SEQ ID NO: 74)

Based on the foregoing, any combination of first and second peptides is contemplated herein, which are formed by reaction of the sidechain —$NH_2$, —OH, or —SH group (e.g., on Lys, Arg, Ser, Thr, or Cys) with the C-terminal carboxyl group, thereby forming a —NH—C(O)— bond or —O—C(O)— bond or —S—C(O)— bond, respectively. Exemplary branched peptides of the invention include, without limitation:

Nap-FFK($^\varepsilon$G-KDDDDKYD-$NH_2$)Y,
Nap-ffk($^\varepsilon$G-KDDDDKYD-$NH_2$)y,
Nap-FFK($^\varepsilon$G-RDDDDKYD-$NH_2$)Y,
Nap-ffk($^\varepsilon$G-RDDDDKYD-$NH_2$)y,
Nap-FFK($^\varepsilon$G-KDDDDKYD-$NH_2$)(Dmt),
Nap-ffk($^\varepsilon$G-KDDDDKYD-$NH_2$)(dmt),
Nap-FFK($^\varepsilon$G-RDDDDKYD-$NH_2$)(Dmt),
Nap-ffk($^\varepsilon$G-RDDDDKYD-$NH_2$)(dmt),
Nap-FFK($^\varepsilon$G-KDDDDK(Dmt)D-$NH_2$)Y,
Nap-ffk($^\varepsilon$G-KDDDDK(Dmt)D-$NH_2$)y,
Nap-FFK($^\varepsilon$G-RDDDDK(Dmt)D-$NH_2$)Y,
Nap-ffk($^\varepsilon$G-RDDDDK(Dmt)D-$NH_2$)y,
Nap-FFK($^\varepsilon$G-KDDDDK(Dmt)D-$NH_2$)(Dmt),
Nap-ffk($^\varepsilon$G-KDDDDK(Dmt)D-$NH_2$)(dmt),
Nap-FFK($^\varepsilon$G-RDDDDK(Dmt)D-$NH_2$)(Dmt),
Nap-ffk($^\varepsilon$G-RDDDDK(Dmt)D-$NH_2$)(dmt),
Nap-FFK($^\varepsilon$G-KDDDDKYD-$NH_2$)Y—Z,
Nap-ffk($^\varepsilon$G-KDDDDKYD-$NH_2$)y-Z,
Nap-FFK($^\varepsilon$G-RDDDDKYD-$NH_2$)Y—Z,
Nap-ffk($^\varepsilon$G-RDDDDKYD-$NH_2$)y-Z,
Nap-FFK($^\varepsilon$G-KDDDDKYD-$NH_2$)(Dmt)-Z,
Nap-ffk($^\varepsilon$G-KDDDDKYD-$NH_2$)(dmt)-Z,
Nap-FFK($^\varepsilon$G-RDDDDKYD-$NH_2$)(Dmt)-Z,
Nap-ffk($^\varepsilon$G-RDDDDKYD-$NH_2$)(dmt)-Z,
Nap-FFK($^\varepsilon$G-KDDDDK(Dmt)D-$NH_2$)Y—Z,
Nap-ffk($^\varepsilon$G-KDDDDK(Dmt)D-$NH_2$)y-Z,
Nap-FFK($^\varepsilon$G-RDDDDK(Dmt)D-$NH_2$)Y—Z,
Nap-ffk($^\varepsilon$G-RDDDDK(Dmt)D-$NH_2$)y-Z,
Nap-FFK($^\varepsilon$G-KDDDDK(Dmt)D-$NH_2$)(Dmt)-Z,
Nap-ffk($^\varepsilon$G-KDDDDK(Dmt)D-$NH_2$)(dmt)-Z,
Nap-FFK($^\varepsilon$G-RDDDDK(Dmt)D-$NH_2$)(Dmt)-Z,
Nap-ffk($^\varepsilon$G-RDDDDK(Dmt)D-$NH_2$)(dmt)-Z, where Z is a therapeutic agent covalently bonded to the C-terminal residue of the first peptide chain, and where Dmt is 2,6-dimethyl-L-tyrosine and dmt is 2,6-dimethyl-D-tyrosine. To the extent that specific embodiments are not otherwise listed above, it is explicitly contemplated that each of the peptides listed above as containing L-amino acids can also be prepared in the form of its D-amino acid enantiomer. For each peptide listed above as containing a mixture of L- and D-amino acids, it is also explicitly contemplated that each of those peptides can be prepared in the form containing only L-amino acids or only D-amino acids.

The branched peptide of the present invention can be prepared by synthesizing protected first and second peptide chains, which are then reacted together using suitable solid-phase or liquid phase peptide coupling conditions, whereby the C-terminus of the second peptide chain (bearing —COOH group) is reacted with the exposed sidechain of the first peptide chain (bearing reactive —$NH_2$ group, OH group, or —SH group) to form the branched peptide. Thereafter, the branched peptide can be de-protected and purified using standard procedures.

Combinations of two or more branched peptides are contemplated herein, including where one branched peptide is un-derivatized with a therapeutic agent and one or more additional branched peptides that are derivatized with the same or different therapeutic agents; or where two or more branched peptides are un-derivatized with a therapeutic agent; or where each of two or more branched peptides are derivatized with the same or different therapeutic agents, and no branched peptide that is un-derivatized with a therapeutic agent is present.

Another aspect of the invention relates to a pharmaceutical composition that includes the branched peptide, as described herein, in an aqueous medium.

In certain embodiments the branched peptides in the pharmaceutical composition form micelle structures. Additionally, the pharmaceutical composition can further contain a therapeutic agent encapsulated within the micelle structures. These therapeutic agents can be hydrophobic.

Exemplary therapeutic agents include, but are not limited to, the following: analgesics, anti-inflammatory agents, anti-helminthics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-thrombogenic agents, anti-claudication agents, anti-atherosclerotic drugs, vascular agents, anti-malarials, anti-migraine agents, anti-muscarinic agents, anti-neoplastic agents (e.g., antiproliferative or chemotherapeutic agents), erectile dysfunction improvement agents, immunosuppressants, anti-protozoal agents, anti-thyroid agents, anxiolytic agents, sedatives, hypnotics, neuroleptics, β-blockers, cardiac inotropic agents, corticosteroids, diuretics, anti-parkinsonian agents, gastro-intestinal agents, histamine receptor antagonists, keratolyptics, lipid regulating agents, anti-anginal agents, Cox-2 inhibitors, leukotriene inhibitors, macrolides, muscle relaxants, nutritional agents, opioid analgesics, protease inhibitors, sex hormones, stimulants, anti-osteoporosis agents, anti-obesity agents, cognition enhancers, anti-urinary incontinence agents, anti-benign prostate hypertrophy agents, essential fatty acids, non-essential fatty acids, antioxidants, and mixtures thereof.

Further non-limiting examples of the therapeutic agents in the pharmaceutical composition include: acetretin, albendazole, albuterol, aminoglutethimide, amiodarone, amlodipine, amphetamine, amphotericin B, arginine, atorvastatin, atovaquone, azithromycin, baclofen, beclomethasone, benazepril, benzonatate, betamethasone, bicalutanide, budesonide, bupropion, busulfan, butenafine, calcifediol, calcipotriene, calcitriol, camptothecin, candesartan, capsaicin, captopril, carbamezepine, carotenes, celecoxib, cerivastatin, cetirizine, chlorpheniramine, cholecalciferol, cilazepril, cilostazol, cimetidine, cinnarizine, ciprofloxacin, cisapride, clarithromycin, clemastine, clomiphene, clomipramine, clonidine, clopidogrel, codeine, coenzyme Q10, cyclobenzaprine, cyclosporin, danazol, dantrolene, dexchlorpheniramine, diclofenac, dicoumarol, digoxin, dehydroepiandrosterone, dihydroergotamine, dihydrotachysterol, dirithromycin, donezepil, doxazosin, efavirenz, eprosartan, ergocalciferol, ergotamine, essential fatty acid sources, etodolac, etoposide, famotidine, fenofibrate, fentanyl, fexofenadine, finasteride, fluconazole, flurbiprofen, fluvastatin, fosphenyloin, frovatriptan, fuirazolidone, gabapentin, gemfibrozil, glibenclamide, glipizide, glyburide, glimepiride, griseofulvin, halofantrine, ibuprofen, irbesartan, irinotecan, isosorbide dinitrate, isotretinoin, itraconazole, ivermectin, ketenserin, ketoconazole, ketorolac, lamotrigine, lansoprazole, leflunomide, lisinopril, loperamide, loratadine, losartan, lovastatin, L-thryroxine, lutein, lycopene, medroxyprogesterone, mifepristone, mefloquine, megestrol acetate, methadone, methoxsalen, methyldopa, metronidazole, miconazole, midazolam, miglitol, minoxidil, mitoxantrone, montelukast, moxonidine, nabumetone, nalbuphine, naratriptan, nelfinavir, nifedipine, nil solidipine, nilutanide, nitrofurantoin, nitroglycerin, nizatidine, omeprazole, oprevelkin, oestradiol, oxaprozin, paclitaxel, paracalcitol, paroxetine, pentazocine, pioglitazone, pizofetin, prazosin, pravastatin, prednisolone, probucol, progesterone, pseudoephedrine, pyridostigmine, rabeprazole, raloxifene, rofecoxib, repaglinide, rifabutine, rifapentine, rimexolone, ritanovir, rizatriptan, rosiglitazone, saquinavir, sertraline, sibutramine, sildenafil citrate, simvastatin, sirolimus, spironolactone, sumatriptan, tacrine, tacrolimus, tamoxifen, tamsulosin, targretin, tazarotene, telmisartan, teniposide, terbinafine, terazosin, tetrahydrocannabinol, tiagabine, ticlopidine, tirofibran, tizanidine, topiramate, topotecan, toremitfene, tramadol, tretinoin, troglitazone, trovafloxacin, ubidecarenone, urapidil, valsartan, venlafaxine, verteporfin, vigabatrin, vitamin A, vitamin D, vitamin E, vitamin K, zafirlukast, zileuton, zolmitriptan, zolpidem, zopiclone, pharmaceutically acceptable salts, isomers, and derivatives thereof, and mixtures thereof.

In certain aspects of the invention, the therapeutic agent in the pharmaceutical composition is an antiproliferative or chemotherapeutic drug. Exemplary antiproliferative or chemotherapeutic drugs include, but are not limited to, Abarelix, aldesleukin, Aldesleukin, Alemtuzumab, Alitretinoin, Allopurinol, Altretamine, Amifostine, Anastrozole, Arsenic trioxide, Asparaginase, Azacitidine, β-lapachone, BCG Live, Bevacuzimab, Avastin, Fluorouracil, Bexarotene, Bleomycin, Bortezomib, Busulfan, Calusterone, Capecitabine, Camptothecin, Carboplatin, Carmustine, Celecoxib, Cetuximab, Chlorambucil, Cisplatin, Cladribine, Clofarabine, Cyclophosphamide, Cytarabine, Dactinomycin, Darbepoetin alfa, Daunorubicin, Denileukin, Dexrazoxane, Docetaxel, Doxorubicin (neutral), Doxorubicin hydrochloride, Dromostanolone Propionate, Epirubicin, Epoetin alfa, Erlotinib, Estramustine, Etoposide Phosphate, Etoposide, Exemestane, Filgrastim, floxuridine fludarabine, Fulvestrant, Gefitinib, Gemcitabine, Gemtuzumab, Goserelin Acetate, Histrelin Acetate, Hydroxyurea, Ibritumomab, Idarubicin, Ifosfamide, Imatinib Mesylate, Interferon Alfa-2a, Interferon Alfa-2b, Irinotecan, Lenalidomide, Letrozole, Leucovorin, Leuprolide Acetate, Levamisole, Lomustine, Megestrol Acetate, Melphalan, Mercaptopurine, 6-MP, Mesna, Methotrexate, Methoxsalen, Mitomycin C, Mitotane, Mitoxantrone, Nandrolone, Nelarabine, Nofetumomab, Oprelvekin, Oxaliplatin, Paclitaxel, Palifermin, Pamidronate, Pegademase, Pegaspargase, Pegfilgrastim, Pemetrexed Disodium, Pentostatin, Pipobroman, Plicamycin, Porfimer Sodium, Procarbazine, Quinacrine, Rasburicase, Rituximab, Sargramostim, Sorafenib, Streptozocin, Sunitinib Maleate, Talc, Tamoxifen, Temozolomide, Teniposide, VM-26, Testolactone, Thioguanine, 6-TG, Thiotepa, Topotecan, Toremifene, Tositumomab, Trastuzumab, Tretinoin, ATRA, Uracil Mustard, Valrubicin, Vinblastine, Vincristine, Vinorelbine, Zoledronate, and Zoledronic acid.

In certain embodiments the therapeutic agent of the pharmaceutical composition is a protein or polypeptide. The protein or polypeptide can be a cytokine or growth factor (such as VEGF, FGF, MCP-1, PlGF, KGF, PDGF), or an antibody or binding portion thereof.

In a further embodiment, the therapeutic agent of the pharmaceutical composition is a radioprotective agent. Exemplary radioprotective agents include, but are not limited to, amifostine, growth factors as their derivatives such as PDGF and KGF (Palifermin=KGF derivative), manganese superoxide dismutase transgene delivery, tetracycline, p53 Up-regulated modulator of apoptosis ("PUMA") inhibitors (Mustata et al., *Curr Top Med Chem* 11(3):281-90 (2011); Greenberger et al., *Front Oncol* 1:59 (2011), each of which is hereby incorporated by reference in its entirety), BEB55, genistein (4',5,7-trihydroxyisoflavone), ACE inhibitors such as captopril and perindopril, 3,3'-diindolylmethane (DIM), ON01210 (a chlorobenzylsulfone derivative known as Ex-RAD), gamma-tocotrienol (GT3), 6-tocotrienol, R-spondin1 (Rspo1), flagellin and flagellin variants such as CBLB502/Entolimod™, interleukins such as IL2 and IL6, and cytokines such as tumor necrosis factor and transforming growth factor-β3.

In certain embodiments, the therapeutic agent of the pharmaceutical composition is a cardioprotective agent selected from the group of α1 adrenoceptor antagonist, α2 blocker, anti-hypotensive agent, angiotensin receptor blockers/ACE inhibitor, angiotensin-1 blockers, endopeptidase, β2 agonists, β2 blockers, diuretics, calcium channel blockers, anti-arrhythmic agents, anti-angiogenic agents, a corticosteroid, VEGF antagonists, and a statin. Non-limiting exemplary cardioprotective agents are prazosin, terazosin, doxazosin, ketenserin, urapidil, arginine, nitroglycerin, clonidine, methyldopa, moxonidine, hydralazine minoxidil, benezepril, captopril, cilazepril, enalapril, fosinopril, lisinopril, perindopril, quinapril, ramipril, trandolapril, zofenopril, candesartan, eprosartan, irbesartan, losartan, telmisartan, valsartan, omapatrilate, acebutolol, atenolol, bisoprolol, celiprolol, esmodol, metoprolol, nebivolol, betaxolol, carvedilol, labetalol, oxprenolol, pindolol, propanolol, chlortalidon, chlorothiazide, epitizide, hydrochlorthiazide, indapamide, amiloride, triamterene, amlodipin, barnidipin, diltiazem, felodipin, isradipin, lacidipin, lercanidipin, nicardipin, nifedipin, nimodipin, nitrendipin, verapamil, amiodarone, solatol, diclofenac, enalapril, flecainide, ciprofloxacin, latanoprost, flucloxacillin, rapamycin and analogues, triamcinolone acetonide, dexamethasone, fluocinolone acetonide, bevacizumab, ranibizumab, pegaptanib, atorvastatin, fluvastatin, lovastatin, pravastatin, rosuvastatin, simvastatin, and pitavastatin.

In a further embodiment, the therapeutic agent of the pharmaceutical composition is an antioxidant, a coenzyme, a vitamin, a metabolite, or a mineral.

In certain embodiments, the branched peptide of the pharmaceutical composition is present at a concentration of from about 100 nM to about 500 μM. Furthermore, the therapeutic agent can be present in an amount from about 1 nM to about 10 μM. Single doses of the pharmaceutical composition may contain from 0.1 μg to 0.1 g of the branched peptide, preferably 4 μg to 0.04 g or 400 μg to 0.4 g; and any effective amount of the therapeutic agent. Typically, single doses of the therapeutic agent range from 1 μg/kg·body weight to 1000 mg/kg·body weight (although lesser or greater dosages are also contemplated).

In some embodiments, the carrier is an aqueous medium. In one embodiment, the aqueous medium is a sterile isotonic aqueous buffer, which is typically well tolerated for administration to an individual. Additional exemplary aqueous media include, without limitation, normal saline (about 0.9% NaCl), phosphate buffered saline ("PBS"), sterile water/distilled autoclaved water ("DAW"), as well as cell growth medium (e.g., MEM, with or without serum), aqueous solutions of dimethyl sulfoxide ("DMSO"), polyethylene glycol ("PEG"), and/or dextran (less than 6% per by weight).

To improve patient tolerance to administration, the pharmaceutical composition may have a pH of about 4.5 to about 8.5. In some embodiments, sodium hydroxide or hydrochloric is added to the pharmaceutical composition to adjust the pH.

In other embodiments, the pharmaceutical composition includes a weak acid or salt as a buffering agent to maintain pH. Citric acid has the ability to chelate divalent cations and can thus also prevent oxidation, thereby serving two functions as both a buffering agent and an antioxidant stabilizing agent. Citric acid is typically used in the form of a sodium salt, typically 10-500 mM. Other weak acids or their salts can also be used.

The pharmaceutical composition may also include solubilizing agents, preservatives, stabilizers, emulsifiers, and the like. A local anesthetic (e.g., lidocaine, benzocaine, etc.) may also be included in the compositions, particularly for injectable forms, to ease pain at the site of the injection.

Another aspect of the present invention relates to enzymatic cleavage products of the branched peptides, whereby cleavage of the second peptide chain disrupts the ability of the (resulting cleaved) branched peptide to form micelle structures. Instead, given the loss of a portion of the second peptide chain from the branched peptide, the resulting product is capable of self-assembly to form nanofibers and possibly larger hydrogel assemblies containing those nanofibers.

Thus, in one embodiment, the invention relates to a nanofiber formed in an aqueous medium which includes self-assembled, enzymatically modified forms of the branched peptide as described herein. As used herein, the term "nanofiber" is defined as a fiber of material having any shape wherein at least one dimension, e.g. the diameter, width, thickness, and the like, is about 100 nm or less. Nanofiber diameters may be about 50 nm or less, about 40 nm or less, about 30 nm or less, about 20 nm or less, about 10 nm or less, about 5 nm or less, about 4 nm or less, about 3 nm or less, about 2 nm or less, or about 1 nm or less in diameter. Although the peptides of the present invention, upon self-assembly, as described herein, form nanofibers, persons of skill in the art should appreciate that such peptides may also form microfibrils that are larger than 100 nm thick.

In another embodiment, the invention relates to a supramolecular hydrogel formed in an aqueous medium that includes a self-assembled, enzymatically modified form of the branched peptide.

In these embodiments, the nanofiber or supramolecular hydrogel includes the enzymatically modified form of the branched peptide as described above. Exemplary enzymatically modified forms of the branched peptides include, without limitation, the following: Nap-FFK($^{e}$G)Y, Nap-FFFK($^{e}$G)Y, Nap-FFGK($^{e}$G)Y, Nap-FFGK($^{e}$G), Nap-FFGK($^{e}$G)F, Nap-ffk($^{e}$G)y, Nap-fffk($^{e}$G)y, Nap-ffgk($^{e}$G)y, Nap-ffgk($^{e}$G), Nap-ffgk($^{e}$G)f, Nap-FFK($^{e}$G)(Dmt), Nap-FFFK($^{e}$G)(Dmt), Nap-FFGK($^{e}$G)(Dmt), Nap-ffk($^{e}$G)(dmt), Nap-fffk($^{e}$G)(dmt), Nap-ffgk($^{e}$G)(dmt), Nap-FFC($^{e}$G)Y, Nap-FFFC($^{e}$G)Y, Nap-FFGC($^{e}$G)Y, Nap-FFGC($^{e}$G), Nap-FFGC($^{e}$G)F, Nap-ffc($^{e}$G)y, Nap-fffc($^{e}$G)y, Nap-ffgc($^{e}$G)y, Nap-ffgc($^{e}$G), Nap-ffgc($^{e}$G)f, Nap-FFC($^{e}$G)(Dmt), Nap-FFFC($^{e}$G)(Dmt), Nap-FFGC($^{e}$G)(Dmt), Nap-ffc($^{e}$G)(dmt), Nap-fffc($^{e}$G)(dmt), and Nap-ffgc($^{e}$G)(dmt), and where the nanofiber or supramolecular hydrogel optionally includes an enzymatically unmodified form of the branched peptide, which may be incorporated into the same.

In addition, where combinations of branched peptides are present in the pharmaceutical composition, then nanofibers and supramolecular hydrogels formed by the enzymatically modified forms of the branched peptides may also include combinations thereof. These nanofibers and supramolecular hydrogels that contain combinations of enzymatically modified forms of the branched peptides may or may not contain a tethered therapeutic agent (Z).

Based on the various combinations of therapeutic agents, both tethered and micelle-containing, and combinations thereof, the branched peptides can be used to deliver the therapeutic agents in patients for the treatment of various disease conditions.

Therefore, one aspect of the invention relates to a method of delivering a therapeutic agent into mitochondria comprising encapsulating a therapeutic agent within a micelle structure of a pharmaceutical composition as described herein, and then contacting a cell with the pharmaceutical composition, whereby micelle structures are taken up by the cell and targeted to mitochondria within the cell. When the micelle structure is altered by way of enzymatic cleavage of the second peptide chain, the micelle-delivered therapeutic agent is released into the contacted cell adjacent to the mitochondria.

Some embodiments of the method relate to the delivering of a therapeutic agent into mitochondria wherein the cell is ex vivo or in vivo. For in vivo contact to occur, a pharmaceutical composition of the invention is administered to an individual administering is carried out parenterally, subcutaneously, intravenously, intradermally, intramuscularly, intraperitoneally, by implantation, by intracavitary or intravesical instillation, intraarterially, intralesionally, intradermally, peritumorally, intratumorally, or by introduction into one or more lymph nodes. Other modes of administration that are effective to present the micelle to cells that are intentionally targeted (i.e., for delivery of the therapeutic agent) can also be used.

Administration of the pharmaceutical composition can be repeated on a daily schedule (i.e., once, twice, or thrice daily), or according to a periodic schedule (i.e., once weekly, bimonthly, once monthly).

Individuals that can be treated include both veterinary patients, typically but not exclusively mammals, as well as human patients.

A further aspect of the invention relates to a method of treating a patient having a cancerous condition. This method includes administering a pharmaceutical composition as described herein to a patient having a cancerous condition, where the administering is effective to inhibit cancer cell survival. Modes and frequency of administration, and patient groups include those identified above.

The cancerous conditions to be treated in accordance with this aspect can involve cancer cells present in a solid tumor, present as a metastatic cell, or present in a heterogenous population of cells that includes both cancerous and non-cancerous cells. Exemplary cancer conditions include, without limitation, cancers or neoplastic disorders of the brain and CNS (glioma, malignant glioma, glioblastoma, astrocytoma, multiforme astrocytic gliomas, medulloblastoma, craniopharyngioma, ependymoma, pinealoma, hemangioblastoma, acoustic neuroma, oligodendroglioma, meningioma), pituitary gland, breast (Infiltrating, Pre-invasive, inflammatory cancers, Paget's Disease, Metastatic and Recurrent Breast Cancer), blood (Hodgkin's Disease, Leukemia, Multiple Myeloma, Lymphoma), lymph node cancer, lung (Adenocarcinoma, Oat Cell, Non-small Cell, Small Cell, Squamous Cell, Mesothelioma), skin (melanoma, basal cell, squamous cell, Kaposi's Sarcoma), bone cancer (Ewing's Sarcoma, Osteosarcoma, Chondrosarcoma), head and neck (laryngeal, pharyngeal, and esophageal cancers), oral (jaw, salivary gland, throat, thyroid, tongue, and tonsil cancers), eye, gynecological (Cervical, Endrometrial, Fallopian, Ovarian, Uterine, Vaginal, and Vulvar), genitourinary (Adrenal, bladder, kidney, penile, prostate, testicular, and urinary cancers), and gastrointestinal (appendix, bile duct (extrahepatic bile duct), colon, gallbladder, gastric, intestinal, liver, pancreatic, rectal, and stomach cancers).

In this aspect of the invention, the pharmaceutical composition contains the branched peptide in combination with a cancer therapeutic agent of the type described above, where the cancer therapeutic agent is tethered to the first peptide chain, introduced separately to the pharmaceutical composition and encapsulated within the micelle structure, both are used together to deliver different forms of the same therapeutic agent (i.e., tethered and untethered forms of the same active agent), or both are used to deliver two different therapeutic agents in combination (i.e., one therapeutic agent tethered and the other untethered but encapsulated within the micelle structure).

While any class of antineoplastic agent, anticancer drug, or chemotherapeutic drug is contemplated for use in connection with the present invention, exemplary agents within these classes include alkylating agents, platinum drugs, antimetabolites, anthracycline and nonanthracycline antitumor antibiotics, topoisomerase inhibitors, mitotic inhibitors, corticosteroids and targeted cancer therapies (such as imatinib, Gleevec®; gefitinib, Iressa®; sunitinib, Sutent®; and bortezomib, Velcade®).

A further aspect of the invention relates to a method of treating an individual exposed to radiation. This method includes administering a pharmaceutical composition as described herein to an individual exposed to, or about to be exposed to, radiation, where the administering is effective to inhibit radiation-induced damage to cells of the individual. Modes and frequency of administration, and patient groups include those identified above. More particularly, administration prior to radiation and/or after radiation exposure is contemplated, including two or more rounds of treatment prior to radiation and two or more rounds of treatment after exposure to radiation. For multiple radiation treatments, the same or different schedule for administration of the pharmaceutical compositions as described herein can be used.

In this aspect of the invention, different forms of the pharmaceutical composition (i.e., containing different therapeutic agents) can be administered at different times. For example, a pharmaceutical composition containing a first therapeutic agent (i.e., with either a tethered or micelle encapsulated therapeutic agent) can be administered prior to radiation, and a second therapeutic agent (i.e., with either a tethered or micelle encapsulated therapeutic agent) can be administered following radiation. In this way, combinations of therapeutic agents that maximize recovery and minimize side effects associated with radiation can be utilized.

Yet another aspect of the invention relates to a method of treating a patient for a cardiovascular disease or condition. This method includes administering a pharmaceutical composition as described herein to an individual having a cardiovascular disease or condition, where the administering is effective to treat the cardiovascular disease or condition. Modes and frequency of administration, and patient groups include those identified above.

Exemplary types of cardiovascular disease or conditions include, but are not limited to, atherosclerosis, arrhythmia, cardiomyopathy, coronary heart disease, infarction, angina, hemorrhagic stroke, ischemic stroke, hypertension, heart failure, peripheral artery disease.

In this aspect of the invention, the pharmaceutical composition contains the branched peptide in combination with a therapeutic agent suitable for treating a cardiovascular disease or condition, including those described above, where the therapeutic agent is tethered to the first peptide chain, introduced separately to the pharmaceutical composition and encapsulated within the micelle structure, both are used together to deliver different forms of the same therapeutic agent (i.e., tethered and untethered forms of the same active agent), or both are used to deliver two different therapeutic agents in combination (i.e., one therapeutic agent tethered and the other untethered but encapsulated within the micelle structure).

EXAMPLES

The examples below are intended to exemplify the practice of embodiments of the disclosure but are by no means intended to limit the scope thereof.

Materials and Methods for Examples 1-5

Materials: All amino acid derivatives involved in the synthesis were purchased from GL Biochem (Shanghai) Ltd. N, N-diisopropylethylamine (DIPEA), 0-benzotriazole-N,N, N',N'-tetramethyluronium-hexafluorophosphate (HBTU) were purchased from Fisher Scientific. The synthesis of all peptide fragments was based on solid-phase peptide synthesis (SPPS). The branched peptides were made via the combination of SPPS and liquid phase synthesis. All crude compounds were purified by HPLC with the yield of 70-80%. All reagents and solvents were used as received without further purification unless otherwise stated.

Minimum Essential Medium (MEM) for HeLa and U87MG cells culture were purchased from ATCC, fetal bovine serum (FBS) and penicillin/streptomycin from Gibco/Life Technologies, and 3-(4,5-Dimethylthiazol-2-yl)-2,5-diphenyltetrazolium bromide (MTT) from ACROS Organics.

Mitochondria isolation kit was purchased from Sigma-Aldrich. The mitochondria were isolated according to the protocol provided by the company.

Instruments:

All peptides were purified by Water Delta600 HPLC system, equipped with an XTerra C18 RP column. LC-MS was operated on a Waters Acquity Ultra Performance LC with Waters MICRO-MASS detector. $^1$H-NMR spectra were gained on Varian Unity Inova 400 with Deuterated DMSO as solvent. Transmission electron microscope (TEM) images were taken on Morgagni 268 transmission electron microscope. Fluorescent analysis was performed on Shimadzu RF-5301-PC fluorescence spectrophotometer. Fluorescence images were taken by ZEISS LSM 880 confocal laser scanning microscope.

Hydrogel TEM Preparation:

The hydrogel was placed on glow discharge thin carbon-coated copper grids (400 meshes, Pacific Grid-Tech) and incubated for 30 s at room temperature. 30 seconds later, a large drop of the ddH$_2$O was placed on parafilm and the grid was allowed to touch the water drop with the sample-loaded surface facing the parafilm. The grid was tilted and allowed to gently absorb water from the edge of the grid using a filter paper sliver (repeated 3 times). Immediately after rinsing, staining was performed by placing a large drop of the UA (uranyl acetate, 2% v/v) stain solution on parafilm and allowing the grid to touch the stain solution drop with the sample-loaded surface facing the parafilm. The grid was tilted and allowed to gently absorb the stain solution from the edge of the grid using a filter paper sliver. The grid was air dried and then examined as soon as possible.

Cell/Mitochondria TEM Preparation:

Mitochondria were isolated from treated cells using the mitochondria isolation kit from Sigma-Aldrich according to the manufacturer's instructions, and the mitochondria were then placed on glow discharge thin carbon-coated copper grids (400 meshes, Pacific Grid-Tech) and prepared for TEM imaging using the same rinsing and staining procedures described above.

Statistical Analysis of the Fiber Diameters:

Using ImageJ Software and obtained TEM images, fiber diameters were measured from each image. Mean and SD of the fibers was obtained from multiple fiber measurements (80) on each TEM image.

Circular Dichroism Measurement:

The CD spectra were recorded (185-300 nm) using a JASCO 810 spectrometer under a nitrogen atmosphere. The hydrogel (0.4 wt %, 200 µL) was placed evenly on the 1 mm thick quartz cuvette and scanned with 0.1 nm interval for three times. The percentage of secondary structures in different samples was calculated by the programs provided in DichroWeb.

Cell Culture and MTT Assay:

Cell culture was carried out with MESA/Dx5 cells. These cells were cultured in Macyo's 5A medium supplemented with 10% v/v fetal bovine serum, 100 U/mL penicillin and 100 µg/mL streptomycin. The condition for cell culture was 37° C. in a humidified atmosphere of 5% $CO_2$. The MTT assay was carried out using MESA/Dx5 cells seeded in a 96-well plate with a density of $1*10^4$ cells per-well (total medium volume of 100 µL). 24 hours post seeding, after the removal of the medium, solutions with serial of concentrations (5 concentrations) of the branched peptides were added to each well. Cells without the treatment of the micelles were used as the control. At designated time (24/48/72 hours), 10 µL MTT solution (5 mg/mL) was added to each well and incubated at 37° C. for another 4 h, and then 100 µL of SDS-HCl solution was added to stop the reduction reaction and dissolve the purple formazan. The absorbance of each well at 595 nm was measured by a multimode microplate reader. The cytotoxicity assay was performed three times and the average value of the three measurements was taken. All the statistical analysis used mean±SEM.

Fluorescent Microscopy:

Imaging was carried out with HeLa cells. These cells were cultured in MEM medium supplemented with 10% v/v fetal bovine serum, 100 U/mL penicillin and 100 µg/mL streptomycin. The condition for cell culture was 37° C. in a humidified atmosphere of 5% $CO_2$. The imaging was carried out using HeLa cells seeded in a confocal dish with a density of $1*10^5$ cells per-dish (total medium volume of 1 mL). 24 hours post seeding, after the removal of the medium, solutions with specific components were added to each dish. At designed time (2, 4, 24 h), the images of cells in each dish was taken by Zeiss 880 confocal microscope.

Example 1—Synthesis of Branched Peptides

FIG. 1 shows the structure of the designed substrate of ENTK. The symbol "T" is used to represent the branching so that the substrate is denoted as D-1$\overline{\text{T}}$FLAG. The branched peptides consist of (i) the FLAG-tag (DYKDDDDK, SEQ ID NO: 35) (Hopp et al., *Nat. Biotechnol.* 6(10):1204-1210 (1988), which is hereby incorporated by reference in its entirety) as the substrate of ENTK for enzymatic recognition and cleavage, (ii) a self-assembling peptide sequence D-1 composed of a 2-acetylnaphthyl group (Nap), a D-tripeptide (D-Phe-D-Phe-D-Lys (ffk)), and a nitrobenzoxadiazoly-ethylenediamino moiety (NBD-EA, for enhanced fluorescence upon self-assembly (Gao et al., *Nat. Commun.* 3:1033:1-19 (2012), which is hereby incorporated by reference in its entirety)) at the C-terminal of the D-peptide, and (iii) a glycine residue as the spacer amino acid residue at the C-terminus of the FLAG-tag, i.e., between (i) and the lysine side chain of (ii). Using Fmoc-based solid-phase peptide synthesis (Chan & White, eds., *Fmoc Solid Phase Peptide Synthesis*, Oxford University Press (2000), which is hereby incorporated by reference in its entirety), first the peptide segments DYKDDDDKG (SEQ ID NO: 75) and Nap-ffk were produced (FIG. 2). After the synthesis, D-1 was generated by conjugating NBD-EA to the Nap-ffk peptide via C-terminal activation. Subsequently, the C-terminal of DYKDDDDKG (SEQ ID NO: 75) was connected to the side chain of lysine in D-1 using the same activation method. Finally, the removal of all protecting groups and then purification by high pressure liquid chromatography (HPLC) produce the designed branch peptide (i.e., D-1⊤FLAG).

Figure 3:
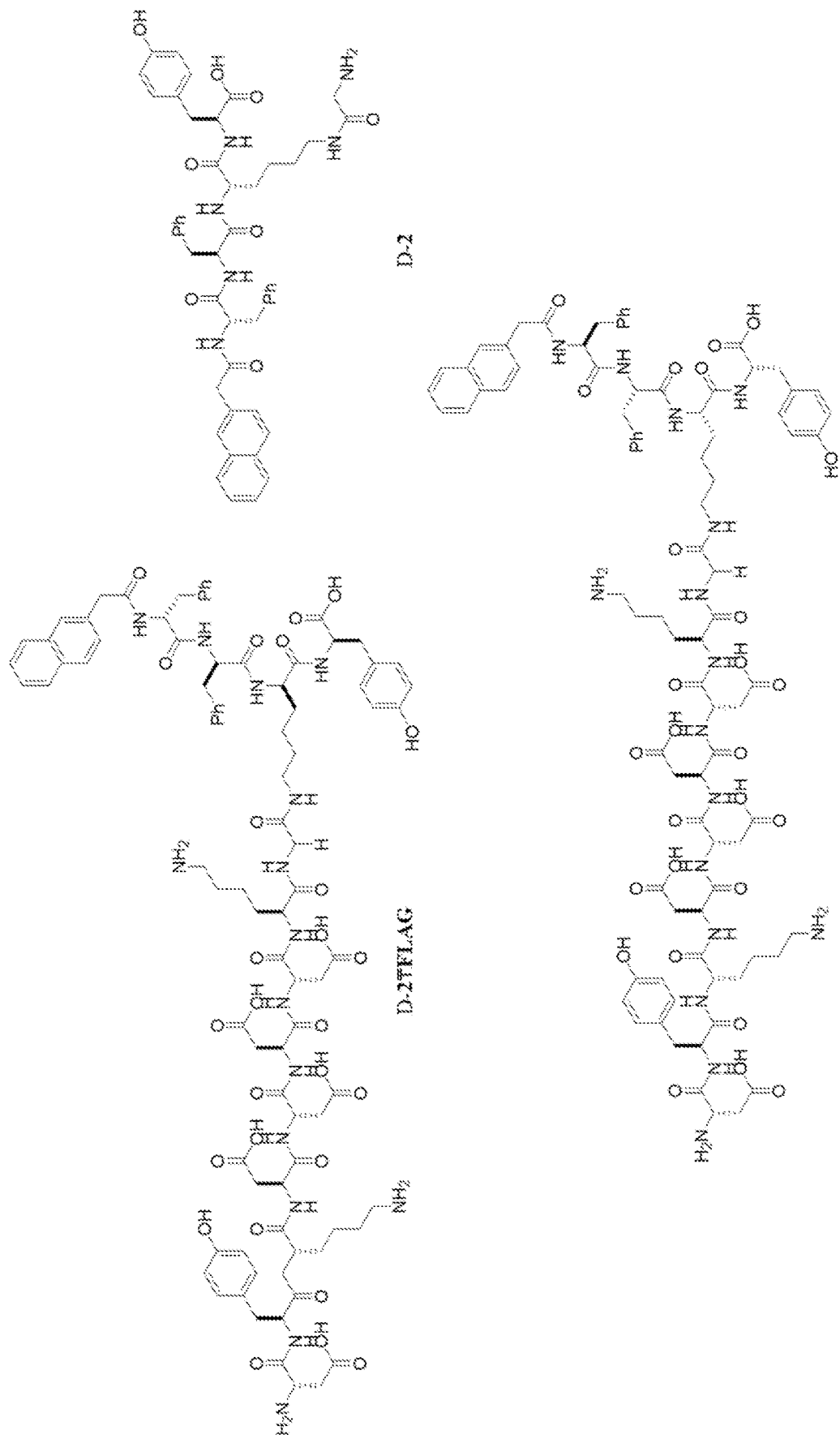
FIG. 3 illustrates the molecular structures of D-2⊤FLAG, D-2, and L-2⊤FLAG.

Similar procedures were performed to produce D-2⊤FLAG and L-2⊤FLAG, which contain the Nap-ffky (D-2) and Nap-FFKY (L-2, SEQ ID NO: 1) sequences without the C-terminal NBD moiety (FIG. 3). In FIG. 3, the $^\varepsilon$Gly moiety is shown linked to the Lys sidechain, forming the —NH—C(O)— bond. Upon coupling the Gly moiety to the C-terminus of DYKDDDDK (SEQ ID NO: 35), protected precursors were formed. Removal of all protecting groups and the purification by high pressure liquid chromatography (HPLC) produce the designed, branched peptides D-2⊤FLAG and L-2⊤FLAG.

Example 2—Self Assembly of Enzyme Activated Peptides

Figure 4:
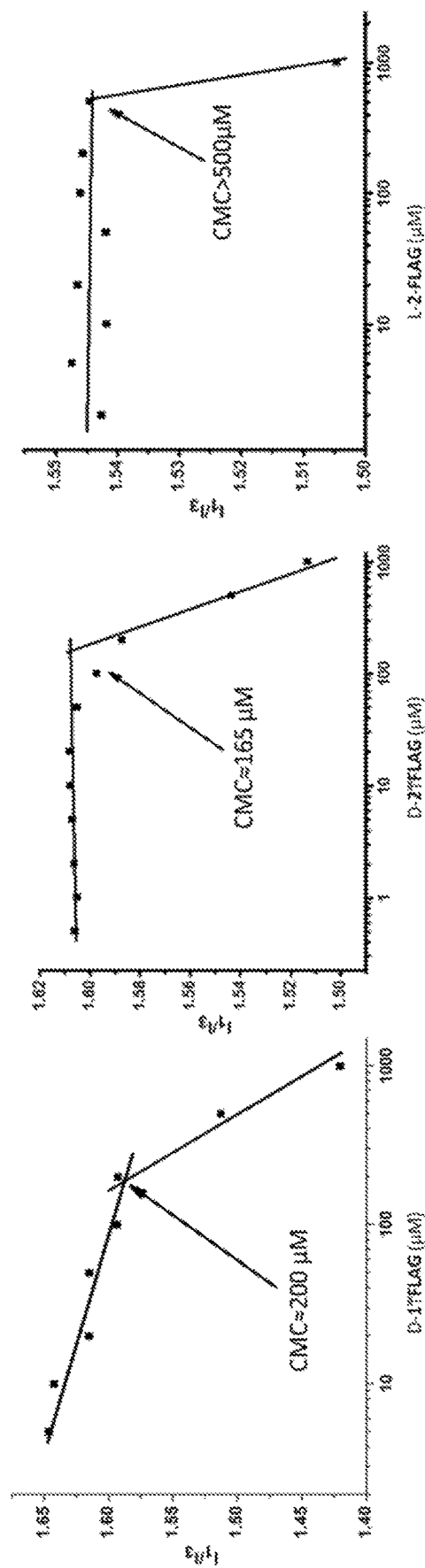
FIG. 4 is the graphical illustration of the critical micelle concentration ("CMC") of D-1⊤FLAG, D-2⊤FLAG and L-2-FLAG in PBS buffer.
Figure 5:
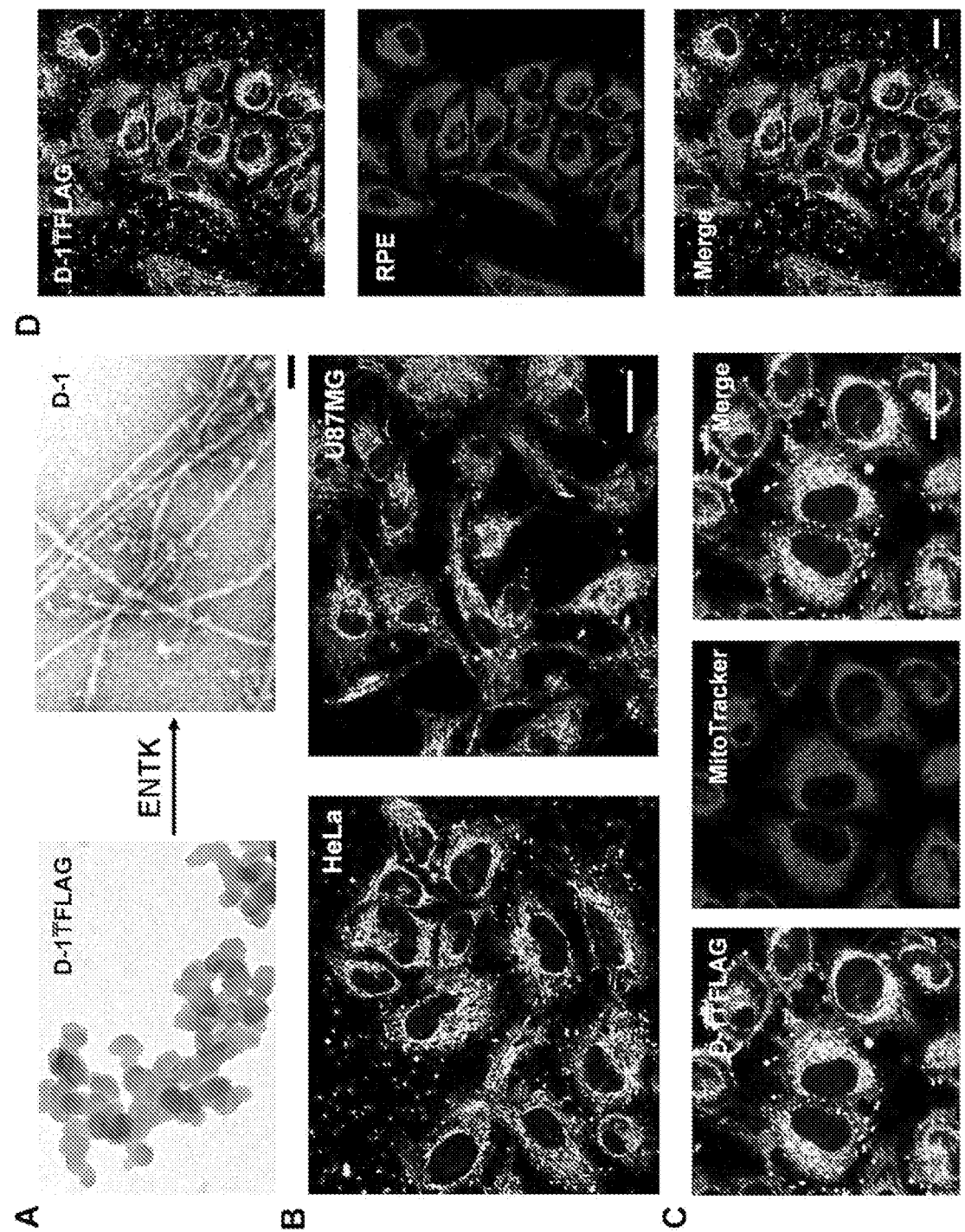
FIGS. 5A-D are representative fluorescent and TEM images of D-1⊤FLAG.

D-1⊤FLAG was dissolved in PBS buffer to a final concentration 200 µM. ENTK (10 U/mL) was added to the solution of D-1⊤FLAG (200 µM), and the solution was incubated at room temperature for 24 h. TEM was then used to observe the micromorphology of D-1⊤FLAG before and after ENTK addition. It was found that D-1⊤FLAG forms nanoparticles (46±11 nm in diameter) at 200 µM (critical micelle concentration (CMC), FIG. 4), which become nanofibers (18±3 nm in diameter) upon the addition of ENTK (FIG. 5A). Circular dichroism (CD) measurement indicates the cleavage of the branch results in largely β-sheet (D-1) and random-coil (FLAG-tag) like secondary structures for the case of D-1⊤FLAG, as well as for those of D-2⊤FLAG and L-2⊤FLAGs (FIG. 3).

Example 3—Cell Uptake of Branched Peptides

200 µM of D-1⊤FLAG was dissolved in MEM medium. HeLa and U87MG cells were incubated with D-1⊤FLAG (200 µM) for 2 h. Zeiss 880 confocal microscope was used to observe the intracellular distribution of D-1⊤FLAG. The mitochondria of HeLa cells were stained by MitoTracker®-DeepRed (Thermofisher Scientific).

After the incubation of HeLa or U87MG cells with D-1⊤FLAG for two hours, fluorescent imaging (FIG. 5B) of these the cells exhibits strong fluorescence, indicating a rapid cellular uptake of D-1⊤FLAG. The preliminary endocytosis study confirms that the uptake of the precursors by HeLa cells likely involves macropinocytosis and clathrin-dependent pathway. Cell viability assay reveals that D-1⊤FLAG exhibits little cytotoxicity to HeLa and U87MG cells, excluding the possibility that the rapid internalization of D-1⊤FLAG originates from the increased membrane permeability caused by cell death (Elmore S., *Toxicol. Pathol.* 35(4):495-516 (2007), which is hereby incorporated by reference in its entirety).

The pattern of the distribution of D-1⊤FLAG in cytosol resembles that of mitochondria (FIG. 5B). Co-staining D-1⊤FLAG with MitoTracker® or Lyso-Tracker® (Thermofisher Scientific) in HeLa cells shows that the fluorescence from D-1⊤FLAG mostly overlaps with the fluorescence of MitoTracker® (FIG. 5C), but co-localizes poorly with the fluorescence from Lysotracker®. These results indicate that D-1⊤FLAG, escaping lysosomes after endocytosis, specifically localizes in mitochondria. However, HeLa cells treated by unbranched D-1 exhibit fluorescence both outside the cells (including membrane) and in the cytosol nonspecifically. Thus, it is inferred that the mitochondria-targeting ability of D-1⊤FLAG likely depends on its unique branching architecture, as well as the electrostatic interaction between the FLAG-tag moiety (negative potential, due to carboxylic groups) and the intermembrane space of mitochondria (positive potential, resulted from abundant $H^+$) (Wikstrom, *Nature* 266(5599):271-273 (1977), which is hereby incorporated by reference in its entirety), as illustrated in FIG. 1.

Notably, D-1⊤FLAG appears to accumulate in the lysosomes of a normal cell line (HS-5), but not the cancer cell lines HeLa, U87MG Saos2, and HepG2.

Example 4—Delivery of Cargo

After mixing R-phycoerythrin (RPE) (1 µg/mL), a protein, with 200 µM D-1⊤FLAG, this mixture, which forms micelles, was used to incubate HeLa cells for two hours. While the control cells (without micelles) show little fluorescence, the cells incubated with RPE and D-1⊤FLAG show fluorescence localized in the mitochondria (FIG. 5D). TEM images of the mixture of RPE and D-1⊤FLAG support the encapsulation of RPE by the micelles (FIG. 6). These results indicate that the micelles formed by D-1⊤FLAG are able to deliver cargo molecules to mitochondria.

Mitochondria targeting of D-1⊤FLAG implies that the micelles formed by other FLAG-tagged precursors made of branched peptides would localize and deliver cargo molecules to mitochondria. Thus, it was examined whether precursors D-2⊤FLAG (also referred to as Mito-FLAG) and L-2⊤FLAG (a diastereomer of D-2⊤FLAG) (see FIG. 3) are able to deliver cargo molecules to mitochondria. The similar CMC values of D-1⊤FLAG and D-2⊤FLAG (FIG. 4) support the interchangeability between them. After mixing RPE, a protein (1 µg/mL), or doxorubicin (Dox) (2 µM), a drug molecule, with L-2⊤FLAG or D-2⊤FLAG (200 µM), the micelles formed were used to incubate HeLa or U87MG cells for two hours. While the control cells (without the micelles formed by the precursors) show little fluorescence, the cells incubated with the micelles and the cargo molecules exhibit strong fluorescence (FIGS. 7A-B), indicating that the intracellular delivery of RPE and Dox by L-2⊤FLAG or D-2⊤FLAG. Similar to D-1⊤FLAG, the patterns of the distribution of RPE (or Dox) inside the cells are akin to that of mitochondria.

To further verify whether the FLAG-tagged precursors deliver cargo molecules to mitochondria specifically, the HeLa cells expressing GFP-Cyt c (Goldstein et al., *Nat. Cell*

Biol. 2(3):156-162 (2000), which is hereby incorporated by reference in its entirety) or Omi-mcherry (Tait et al., *Dev. Cell* 18(5):802-813 (2010), which is hereby incorporated by reference in its entirety) in mitochondria were incubated with RPE or Dox in the presence of D-2$\bar{\text{T}}$ FLAG. Fluorescent images confirm that the fluorescence of RPE or Dox extensively overlaps with that from GFP-cyt c and Omi-mcherry (FIG. 7C). Quantification of the overlap of the fluorescence (Manders et al., *J. Microsc.* 169(3):375-382 (1993), which is hereby incorporated by reference in its entirety) confirms that RPE or Dox alone hardly co-localize with mitochondria, but D-2$\bar{\text{T}}$ FLAG significantly boosts the localization of RPE or Dox in mitochondria (FIG. 7D).

Both D-2$\bar{\text{T}}$ FLAG and L-2$\bar{\text{T}}$ FLAG induce minimal cytotoxicity alone (FIGS. 8A-C). However, Dox, after mixing with D-2$\bar{\text{T}}$ FLAG or L-2$\bar{\text{T}}$ FLAG, exhibits significantly increased cytotoxicity against HeLa cells compared to Dox only. That is, the branched peptide precursors decrease the $IC_{50}$ of Dox from 3.0 μM to 400 nM (FIG. 8D). In addition, D-2$\bar{\text{T}}$ FLAG significantly boosts the activity of Dox against Dox-resistant cancer cell line (MESA/Dx5, (Harker & Sikic, *Cancer Res.* 45(9):4091-4096 (1985), which is hereby incorporated by reference in its entirety) (FIG. 8D). The synergistic effect (FIG. 8E) of Dox and the FLAG-tagged precursors against cancer cells likely originates from the micelles enhancing the uptake of Dox and Dox interfering with mitochondrial DNA. These results confirm the generality that FLAG-tagged branch peptide precursors serve as carriers for delivering cargo molecules to mitochondria.

Example 5—Mechanics of Self-Assembly

To confirm that the nanofibers form at mitochondria after ENTK cleaves the branch of the branched peptides, mitochondria were isolated from HeLa cells incubated with D-2$\bar{\text{T}}$ FLAG (200 μM) for different times. HeLa cells were seeded in a 6 cm petri dish and incubated in a cell incubator (37° C., 5% $CO_2$) until confluence. After that, the HeLa cells were incubated with 200 μM D-2$\bar{\text{T}}$ FLAG (Mito-Flag) dissolved in MEM culture medium, 10% FBS, 1% Pen-strep for another 2 or 24 h. Finally, the mitochondria of HeLa cells were isolated using a mitochondria isolation kit (purchased from Thermofisher) using the procedure provided by the manufacture. TEM was then used to observe the morphology of mitochondria.

The cells treated by D-2$\bar{\text{T}}$ FLAG for 2 h and 24 h produce mitochondria surrounded by nanoparticles and nanofibers, respectively (FIGS. 9A-B), while the mitochondria from the HeLa cells incubated with only culture medium exhibit a surface without either nanoparticles or nanofibers. Western blot analysis of the mitochondria isolated from HeLa and U87MG cells showed two ENTK bands (FIG. 10); the major band is the light chain (Lu et al., *J. Mol. Biol.* 292(2):361-373 (1999), which is hereby incorporated by reference in its entirety), indicating the presence of ENTK on mitochondria. Moreover, LC/MS analysis of the isolated mitochondria confirmed that D-2 is the main component of the nanofibers, indicating that D-2$\bar{\text{T}}$ FLAG, after reaching mitochondria, is cleaved by ENTK. The in situ formation of nanofibers results in the localization of the nanofibers at mitochondria. To verify whether the proteolysis is necessary for mitochondria targeting, the D-peptide control (D-1$\bar{\text{T}}$ flag) was created by connecting D-1 to the D-enantiomer of FLAG tag (flag), which is resistant to ENTK. The fluorescent images of HeLa cells incubated with D-1$\bar{\text{T}}$ flag (200 μM, 2 h) failed to exhibit a mitochondria-specific distribution, confirming that the prevention of proteolysis (the conversion to nanofibers) catalyzed by ENTK abolishes the mitochondria targeting.

Discussion of Examples 1-5

The foregoing Examples demonstrate that branched peptides act as a novel type of substrates for enzymatic self-assembly to target mitochondria. Although carrying multiple negative charges, the FLAG-tagged precursors undergo rapid endocytosis and specifically accumulate in mitochondria. The deposition of the nanofibers affect little on the cellular activity, likely due to that the nanofibers impact less than cationic molecules on the membrane potential of mitochondria. The branch architecture is uniquely important for targeting mitochondria since the linear peptide, L-2-FLAG, was shown to be unable to deliver cargo molecule to mitochondria. This work highlights the importance of reactions, in addition to nanoarchitectonics (Komiyama et al., *Bull. Chem. Soc. Jpn.* 90(9):967-1004 (2017), which is hereby incorporated by reference in its entirety), for controlling biological systems. Contrasting to most of the reported mitochondria targeting molecules that usually are lipophilic and cationic (Hopp et al., Nat. Biotechnol. 6(10): 1204-1210 (1988), which is hereby incorporated by reference in its entirety), this observation illustrates a new mechanism for targeting mitochondria: the integration of enzymatic reaction and self-assembly (i.e., EISA). As a consequence, the branched peptides of the invention may be able to complement other approaches, e.g., triphenyl phosphonium (TPP) (Zielonka et al., *Chem. Rev.* 117(15):10043-10120 (2017); PCT Application No. PCT/US2018/012359, each of which is hereby incorporated by reference in its entirety). Although the targeting of mitochondria relies on ENTK in this work, the strategy demonstrated here should allow the development of the substrates of other enzymes on mitochondria for mitochondria targeting. Among numerous approaches for mitochondria-specific drug delivery (Yamada et al., *Mitochondrion* 7(1-2):63-71 (2007); Schatz G., *J. Biol. Chem.* 271(50):31763-31766 (1996), which are hereby incorporated by reference in their entirety), the delivery of cargo molecules to target mitochondria by the FLAG-tagged precursors is particularly promising and worth further exploration for potential applications in biomedicine because of the cell compatibility of the FLAG-tagged precursors and the biological importance of mitochondria (Green et al., *Science* 345(6203):1466 (2014), which is hereby incorporated by reference in its entirety).

Example 6—Formation of Hydrogels

400 μL of 2.5% wt Mito-Flag (D-2$\bar{\text{T}}$ FLAG) solution was put into a glass vial, followed by the addition of ENTK (final concentration 10 U/ml). The vial with Mito-Flag solution was put into a 37° C. water bath, and incubated for 24 h. The images of hydrogel (FIG. 11) were obtained after 24 h incubation. Transmission electron microscope was used to observe the morphology of Mito-Flag solution (200 μM) before and after ENTK addition.

Example 7—Delivery of Plasmids into Mitochondria Using Mito-Flag

Figure 12:
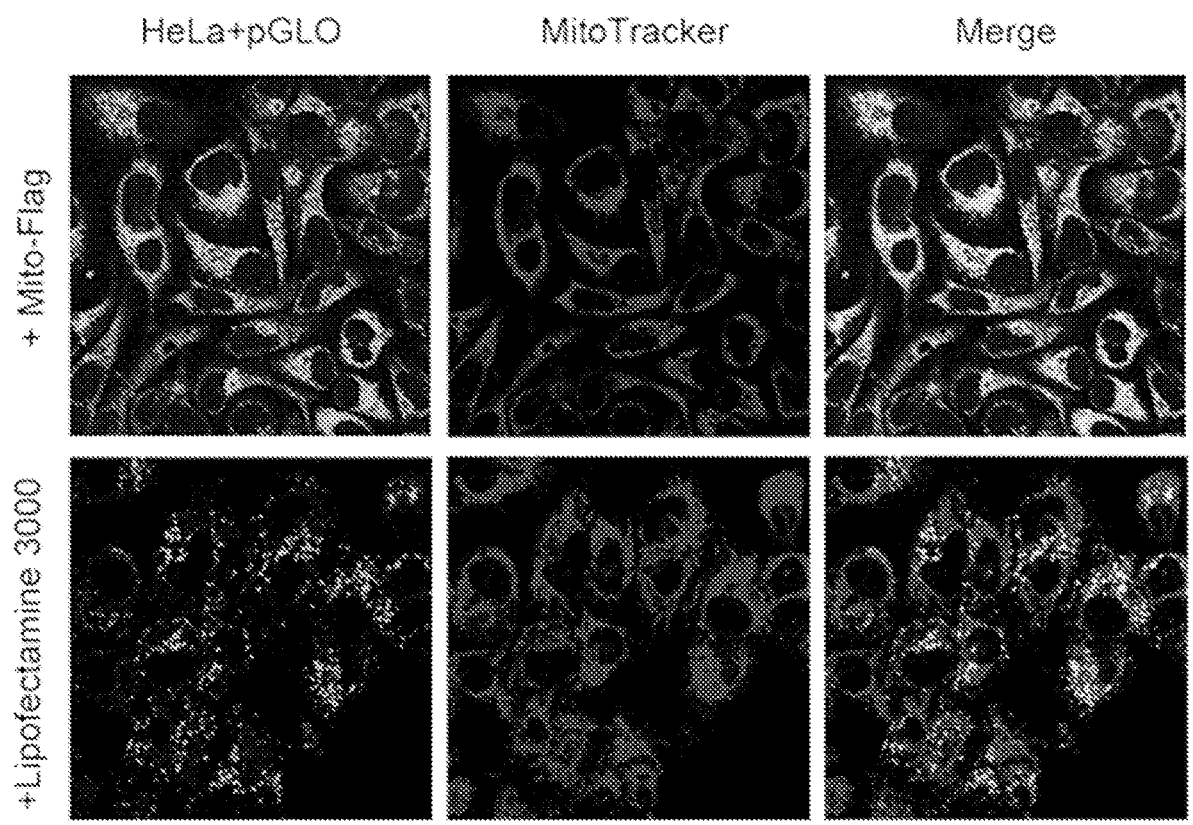
FIG. 12 are fluorescent images of HeLa cells incubated with pGLO plasmid (5 µg/ml) in the presence of Mito-Flag (200 µM) or lipofectamine 3000 for 48 h. The fluorescence from GFP expressed by pGLO plasmid extensively overlap with the fluorescence from MitoTracker®, indicating the delivery of pGLO plasmid into mitochondria.

70% Confluent HeLa cells in experiment groups were incubated with Mito-Flag (D-2$\bar{\text{T}}$ FLAG) (200 μM) in the presence of pGLO plasmid (5 μg/mL). Lipofectamine 3000 was used to deliver pGLO plasmid to HeLa cells (70% confluent) in control groups using the procedure provided by manufacture. The cells were incubated in a cell incubator for another 48 h followed by using a Zeiss 880 confocal microscope to observe the intracellular protein expression of pGLO. As shown in FIG. 12, the fluorescence from GFP expressed by the pGLO plasmid extensively overlaps with the fluorescence from MitoTracker®, indicating the delivery of the pGlo plasmid into the mitochondria.

Figure 13:
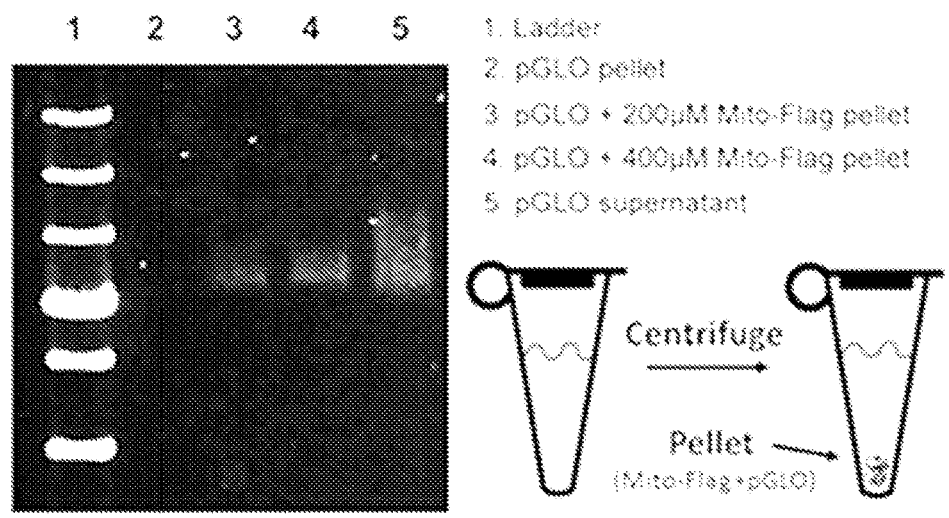
FIG. 13 shows the DNA electrophoresis analysis of pGLO plasmid in the pellet of Mito-Flag (D-2⊤FLAG) after high-speed centrifugation.

DNA electrophoresis analysis of pGLO plasmid in the pellet of Mito-Flag is shown in FIG. 13. 500 µL of 1 µg/mL pGLO was mixed with Mito-Flag at different concentration (0, 200 and 400 µM) in centrifuge tubes. The pGLO plasmids in solutions were then centrifuged down (14000 g, 1.5 h). The pellet at the bottom of centrifuge tubes were collected and dissolved in 10 µL PBS buffer, followed by DNA electrophoresis analysis. 10 µL pGLO solution (1 µg/mL) was used as the positive control.

Figure 14:
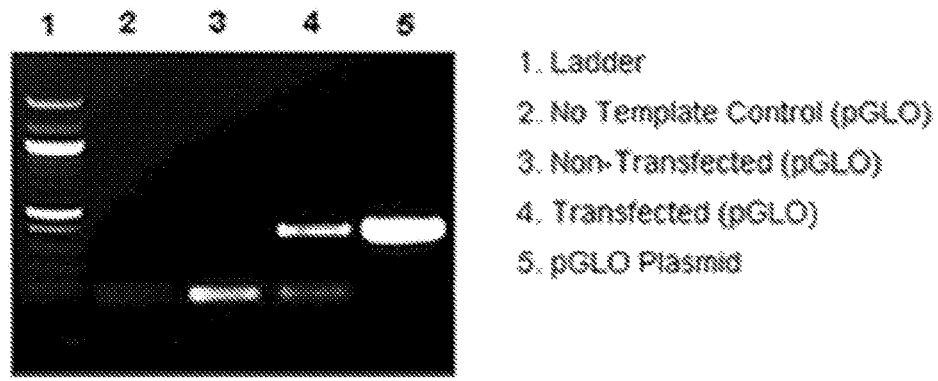
FIG. 14 is an image of the electrophoresis gel used in the detection of pGLO plasmid in the mitochondria isolated from the HeLa cells treated by pGLO (5 µg/ml) and Mito-Flag (D-2⊤FLAG) (200 µM).

The detection of pGLO plasmid from the mitochondria isolated from HeLa cells treated by pGLO and Mito-Flag is shown in FIG. 14. 70% Confluent HeLa cells in experiment groups were incubated with Mito-Flag (200 µM) in the presence of pGLO plasmid (5 µg/mL). The mitochondria were isolated using mitochondria isolation kit (Thermofisher). The isolated mitochondria were then dissolved using a cell lysis buffer. The mitochondria DNA was precipitated by adding ethanol (twice volume) into the previous lysis buffer. The pGLO plasmid in mitochondria was amplified by PCR reaction and detected by DNA electrophoresis.

Example 8—Delivery of Viral Vector into Mitochondria Using Mito-Flag

Figure 15:
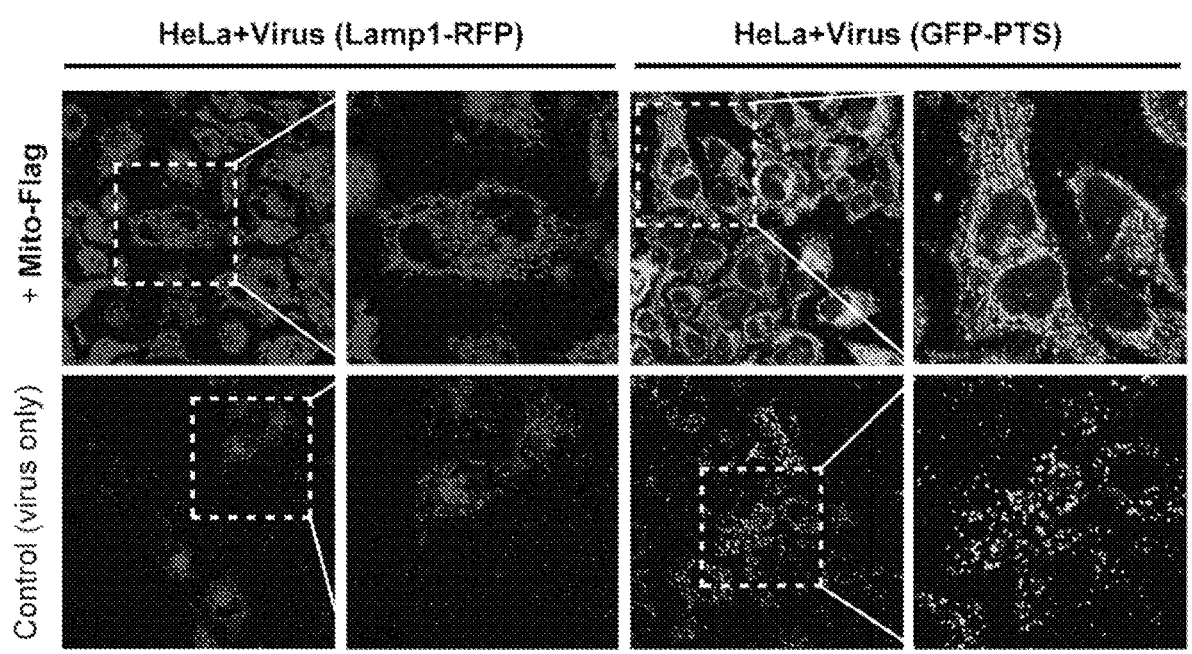
FIG. 15 is a panel of fluorescent images of HeLa cells incubated with baculovirus expressing RFP-Lamp1 (lysosomal associated membrane protein) in the presence of 200 µM Mito-Flag (D-2⊤FLAG) for 24 h

70% Confluent HeLa cells in experiment groups were incubated with Mito-Flag (D-2$\overline{T}$FLAG) (200 µM) in the presence of baculovirus expressing LAMP1-RFP (lysosomal associated membrane protein) and GFP-PTS. Cells were then incubated in a cell incubator for another 24 h, followed by imaging using a Zeiss 880 confocal microscope to observe the intracellular protein expression. The fluorescent images of HeLa cells incubated with baculovirus expressing RFP-Lamp1 and GFP-PST is shown in FIG. 15.

The mitochondria of the transfected (baculovirus-expressing LAMP 1-RFP) HeLa cells were isolated using mitochondria isolation kit (Thermofisher). The HeLa cells were treated with baculovirus expressing RFP-Lamp1 and Mito-Flag (D-2$\overline{T}$FLAG) (200 µM) for 24 h. The mitochondria were then dissolved using a cell lysis buffer, and the LAMP1-RFP in the mitochondria was detected by western blot.

Figure 16:
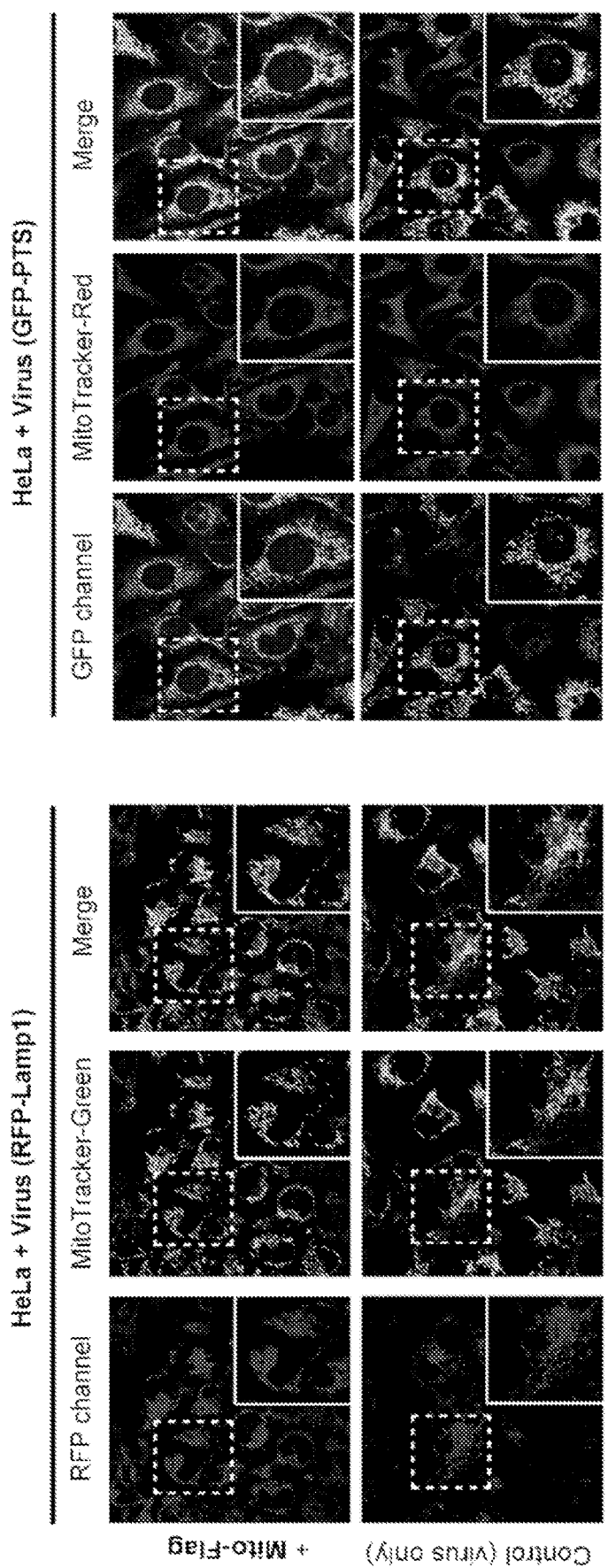
FIG. 16 is a panel of fluorescent images of GFP-Cyt C HeLa and HeLa cells are treated by virus in the presence of 200 µM Mito-Flag (D-2⊤FLAG). The colocalization of RFP-Lamp1 with GFP-Cyt C, and GFP-PTS with MitoTracker confirm that the exogenous fluorescent proteins are expressed in mitochondria.

In further experimentation, 70% Confluent Cyt C-GFP HeLa and normal HeLa cells in experiment groups were incubated with Mito-Flag (D-2$\overline{T}$FLAG) (200 µM) in the presence of baculovirus expressing LAMP1-RFP and GFP-PTS, respectively. The cells were incubated in a cell incubator for another 24 h followed by using a Zeiss 880 confocal microscope to observe the intracellular protein expression. MitoTracker-DeepRed was used to stain the mitochondria in normal HeLa cells. The colocalization (as seen in FIG. 16) of RFP-Lamp1 with GFP-Cyt C, and GFP-PTS with MitoTracker confirm that the exogenous fluorescent proteins are expressed in mitochondria.

Figure 17:
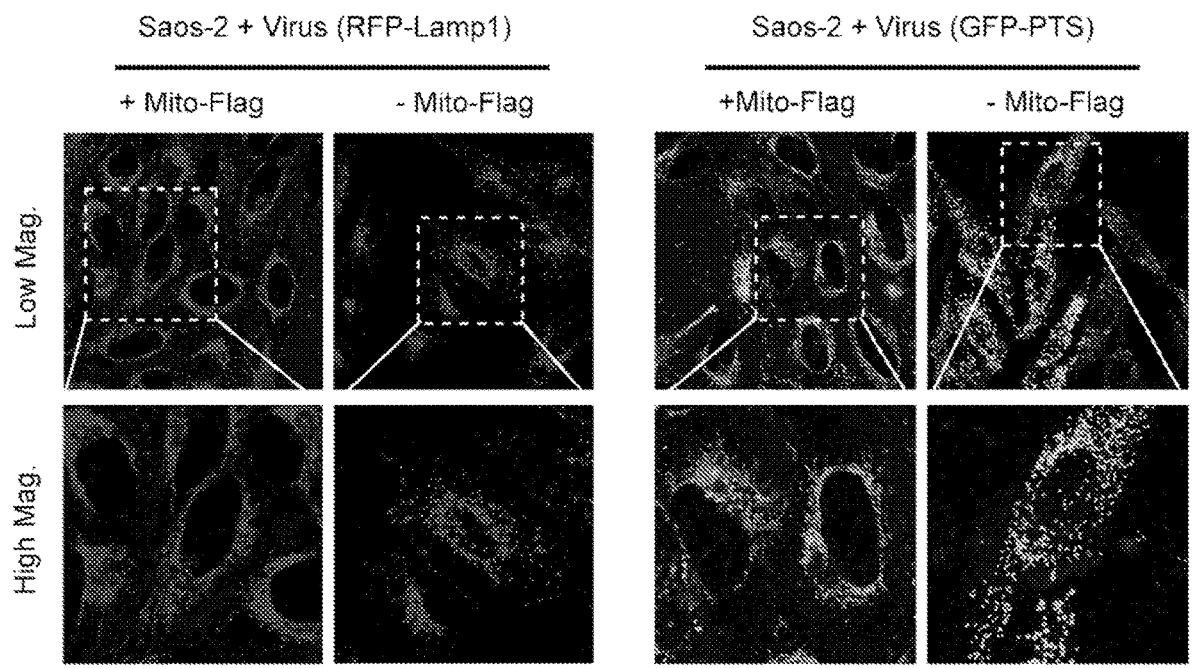
FIG. 17 is a panel of fluorescent images of Saos-2 cells are incubated with virus expressing RFP-Lamp1 and GFP-PTS with 200 μM Mito-Flag (D-2T̄ FLAG).
Figure 18:
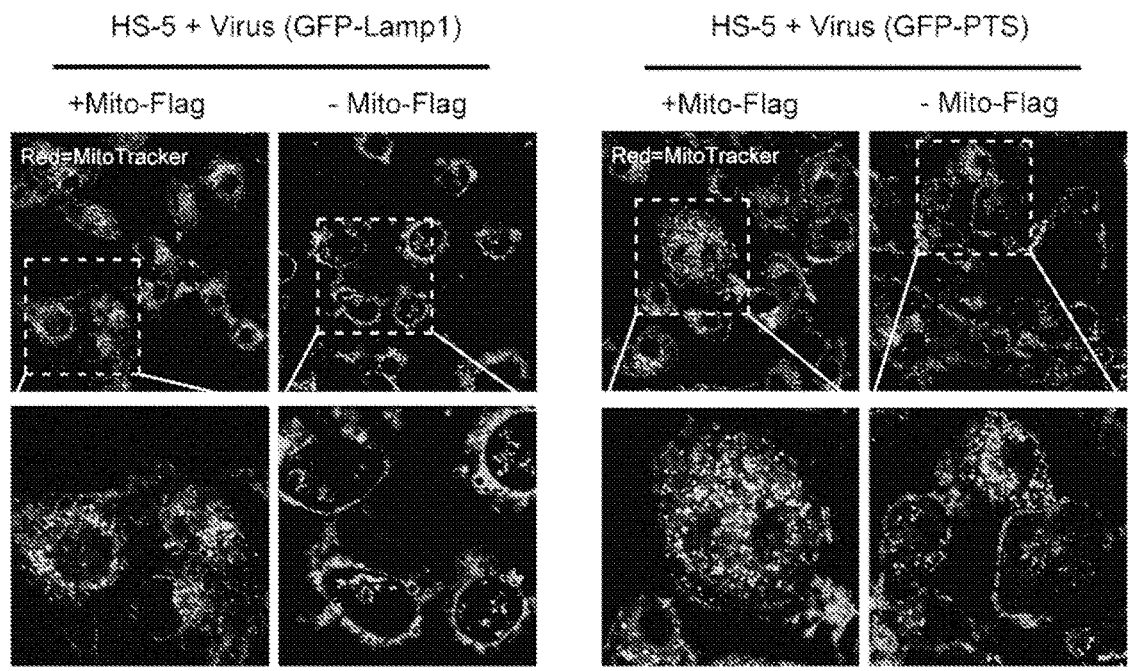
FIG. 18 is a panel of fluorescent images of HS-5 cells are incubated with virus expressing RFP-Lamp1 and GFP-PTS with 200 μM Mito-Flag (D-2T̄ FLAG). The absence of fluorescence in the mitochondria of HS-5 suggests a cancer cell-specific transfection.

Additionally, Saos-2, HepG2, and HS-5 cells were also tested under similar conditions. 70% Confluent Saos-2, HepG2, and HS-5 cells in experiment groups were incubated with Mito-Flag (D-2$\overline{T}$FLAG) (200 µM) in the presence of baculovirus expressing LAMP1-RFP and GFP-PTS. Cells were incubated in a cell incubator for another 24 h followed by using a Zeiss 880 confocal microscope to observe the intracellular protein expression. Image of the Saos-2 Cells are displayed in FIG. 17, and the images of the HS-5 cells are displayed in FIG. 18. The Mitochondria in HS-5 were stained with MitoTracker®-DeepRed (Thermofischer).

Example 9—Gene Transfection with Mito-Flag

In order to test gene transfection, HeLa cells were grouped and treated with two processes. Group ①: 70% confluence HeLa cells were incubated with 200 µM Mito-Flag and baculovirus expressing LAMP1-RFP or GFP-PTS in MEM medium. After 24 h, old medium was removed, and cells were washed with PBS buffer 3 times. Then, HeLa cells were incubated with fresh MEM medium for another 24 h before imaging.

Figure 19:
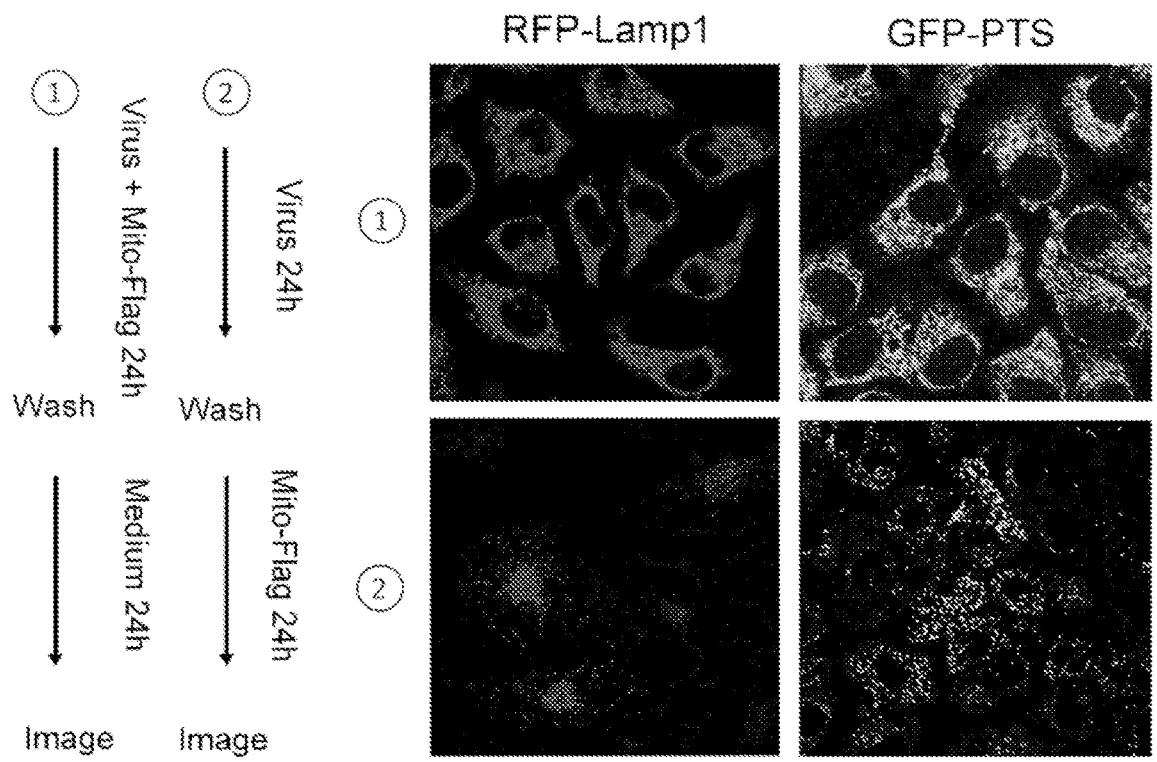
FIG. 19 is a panel of fluorescent images of HeLa cells treated by processes ① and ②. Results indicate that the localizations of Lamp1 and GFP-PTS in mitochondria mostly originate from gene transfection.

Group ②: 70% confluence HeLa cells were incubated with baculovirus expressing LAMP1-RFP or GFP-PTS in MEM medium. After 24 h, old medium was removed, and cells were washed with PBS buffer 3 times. Then, HeLa cells were incubated with fresh MEM medium including 200 µM Mito-Flag for another 24 h before imaging. The results indicate the localization of the LAMP 1-RFP and GFP-PTS in the mitochondria (displayed in FIG. 19) mostly originate from gene transfection.

Figure 20:
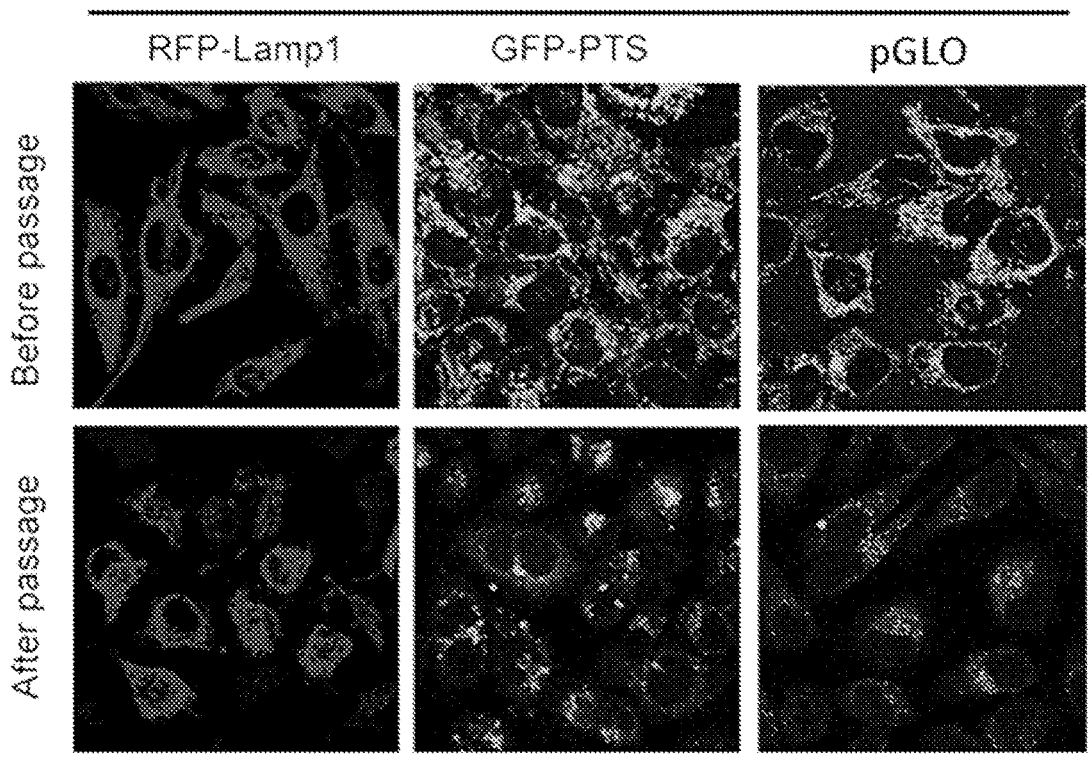
FIG. 20 is a panel of fluorescent images of gene transfected HeLa cells before and after cell passage.

Further, gene transfected HeLa cells were images before and after cell passage, as shown in FIG. 20. To accomplish this, 70% confluence HeLa cells were incubated with 200 µM Mito-Flag in the present of pGLO plasmid (5 µg/mL) or baculovirus expressing LAMP1-RFP or GFP-PTS in MEM medium. After 24 h, cells were passaged and 50% of them were seeded back to new confocal dishes. HeLa cells in new dished were incubated with fresh MEM medium for another 24 hours before imaging. Cells were imaged by Zeiss 880 confocal microscope.

Discussion of Examples 6-9

Cell selective gene expression at mitochondria holds great potentials for treating mitochondrial diseases. But current approaches, including mitochondria transfer, still suffer serious limitations. The preceding Examples 6-9 show that enzymatic morphology/phase transition of isopeptides effectively translocates gene expression to mitochondria in a cell selective manner. Consisting of DYKDDDDK (SEQ ID NO:35) as the branch and phenylalanine rich short peptides as the backbone, the isopeptides form micelles, which, upon the cleavage of the Flag catalyzed by enterokinase, turn into a gel made of nanofibers. The mitochondrial enterokinase cleaves the Flag of the isopeptides, thus turning the micelles to nanofibers on the mitochondria. Mixing the Mito-Flags and a DNA plasmid encoding GFP or baculovirus vectors carrying the genes of proteins translocates the gene expression to mitochondria, evidenced by the exclusive expression of those non-mitochondrial proteins at mitochondria. Using local enzymatic reaction to omit or override signal peptides for mitochondria-targeted gene expression, this work provides a new way to target organelles and may offer a new perspective to understanding cell specific endogenous trafficking.

Most of the reported mitochondria targeting molecules are lipophilic and cationic, which may become cytotoxic with accumulation. The preceding Examples show enzymatic cleavage of branched peptides that carry negative charges for targeting mitochondria. Conjugating a well-established protein tag (i.e., FLAG-tag) to self-assembling motifs affords the precursors that form micelles. Enzymatic cleavage of the hydrophilic FLAG motif (DDDDK) (SEQ ID NO:

17) by enterokinase (ENTK) turns the micelles to nanofibers. After being taken up by cells, the micelles, upon the action of intracellular ENTK, turns into nanofibers to locate mainly at mitochondria. The micelles of the precursors are able to deliver cargos (either small molecules or proteins) into cells, largely to mitochondria and within two hours. Preventing ENTK proteolysis diminishes mitochondria targeting. As the first report of using enzymatic self-assembly for targeting mitochondria and delivery cargos to mitochondria, this work illustrates a fundamentally new way to target subcellular organelles for biomedicine.

Example 10—Prospective Treatment of Uterine Cancer Xenograft Using Dox in Combination with Mito-Flag MES-SA/Dx5 cells are an established model cell-line (human uterine sarcoma) for evaluating the efficacy and toxicity of new drugs in vivo.

Fifteen nude mice will be used for experiments to define the tumor growth curve. $1 \times 10^7$ MES-SA/Dx5 cells will be implanted into the mice via intraperitoneal injection using a 25 G needle. Five of the tumor-bearing mice will be used to define the tumor growth curve with control treatment, five mice will be given DOX (only), and five mice will be given a mixture of DOX/D-2T̄ FLAG. The mice will be injected subcutaneously and peritumorally (6 times, every 3 days starting at Day 1) with either 100 μL of D-2T̄ FLAG at 4 μg/μL (400 μg dose or 40 mg/kg) with 5 mg/kg DOX in PBS buffer (experimental), or 5 mg/kg DOX in 100 μL PBS buffer (experimental), or 100 μL, of PBS buffer (control). Tumor volume measurements will be made every three days, also starting on Day 1. Volume of tumors will be measured by caliper.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A branched peptide comprising:
a first peptide chain and a second peptide chain having its C-terminal amino acid covalently linked to a sidechain of an amino acid residue of the first peptide chain, wherein the first peptide chain comprises a plurality of aromatic amino acids and an aromatic group linked to an amino terminus of the first peptide chain, and comprises the amino acid sequence of napthylacetyl-FFKY (SEQ ID NO: 1), napthylacetyl-FFFKY (SEQ ID NO: 2), napthylacetyl-FFGKY (SEQ ID NO: 3), napthylacetyl-FFGK (SEQ ID NO: 4), FFGKF (SEQ ID NO: 5), napthylacetyl-ffky, napthylacetyl-fffky, napthylacetyl-ffgky, napthylacetyl-ffgk, napthylacetyl-ffgkf, napthylacetyl-FFK(Dmt) (SEQ ID NO: 6), napthylacetyl-FFFK(Dmt) (SEQ ID NO: 7), napthylacetyl-FFGK(Dmt) (SEQ ID NO: 8), napthylacetyl-ffk(dmt), napthylacetyl-fffk(dmt), napthylacetyl-ffgk (dmt), napthylacetyl-FFCY (SEQ ID NO: 9), napthylacetyl-FFFCY (SEQ ID NO: 10), napthylacetyl-FFGCY (SEQ ID NO: 11), napthylacetyl-FFGC (SEQ ID NO: 12), napthylacetyl-FFGCF (SEQ ID NO: 13), napthylacetyl-ffcy, napthylacetyl-fffcy, napthylacetyl-ffgcy, napthylacetyl-ffgc, napthylacetyl-ffgcf, napthylacetyl-FFC(Dmt) (SEQ ID NO: 14), napthylacetyl-FFFC(Dmt) (SEQ ID NO: 15), napthylacetyl-FFGC(Dmt) (SEQ ID NO: 16), napthylacetyl-ffc(dmt), napthylacetyl-fffc(dmt), or napthylacetyl-ffgc(dmt), wherein Dmt is 2,6-dimethyl-L-tyrosine and dmt is 2,6-dimethyl-D-tyrosine; and wherein the second peptide chain comprises a plurality of hydrophilic amino acids and an enzyme cleavage site, and comprises the amino acid sequence of DDDDK (SEQ ID NO: 17), KDDDK (SEQ ID NO: 18), DDDDR (SEQ ID NO: 19), KDDDR (SEQ ID NO: 20), DADDK (SEQ ID NO: 21), KADDK (SEQ ID NO: 22), DADDR (SEQ ID NO: 23), KADDR (SEQ ID NO: 24), DEDDK (SEQ ID NO: 25), KEDDK (SEQ ID NO: 26), DEDDR (SEQ ID NO: 27), KEDDR (SEQ ID NO: 28), EDDDK (SEQ ID NO: 29), EDDDR (SEQ ID NO: 30), EEDDK (SEQ ID NO: 31), EEDDR (SEQ ID NO: 32), DLYDDDDK (SEQ ID NO: 33), DLYDDDDR (SEQ ID NO: 34), DYKDDDDK (SEQ ID NO: 35), DYKDDDDR (SEQ ID NO: 36), DYKDADDK (SEQ ID NO: 37), DYKDADDR (SEQ ID NO: 38), DYKDEDDK (SEQ ID NO: #39), DYKDEDDR (SEQ ID NO: 40), DYKEDDDK (SEQ ID NO: 41), DYKEDDDR (SEQ ID NO: 42), DYKEEDDK (SEQ ID NO: 43), DYKEEDDR (SEQ ID NO: 44), or LKGDR (SEQ ID NO: 45).

2. The branched peptide according to claim 1, wherein the plurality of aromatic amino acids are selected from the group consisting of phenylalanine, tyrosine, and tryptophan.

3. The branched peptide according to claim 1, wherein the amino acid residue having the sidechain covalently linked to the C-terminal amino acid of the second peptide chain is:
(i) Lys, and the covalent bond is —NH—C(O)—; or
(ii) Cys, and the covalent bond is —S—C(O)—.

4. The branched peptide according to claim 1, wherein the first peptide is less than 20 amino acids in length.

5. The branched peptide according to claim 1, wherein the branched peptide is capable of forming micelle structures in an aqueous medium and, following enzymatic cleavage of the second peptide chain at the enzyme cleavage site, is capable of self-assembling to form a hydrogel in an aqueous medium.

6. The branched peptide according to claim 1, wherein the first peptide chain is selected from the group consisting of napthylacetyl-FFKY (SEQ ID NO: 1), napthylacetyl-FFFKY (SEQ ID NO: 2), napthylacetyl-FFGKY (SEQ ID NO: 3), napthylacetyl-FFGK (SEQ ID NO: 4), napthylacetyl-FFGKF (SEQ ID NO: 5), napthylacetyl-ffky, napthylacetyl-fffky, napthylacetyl-ffgky, napthylacetyl-ffgk, napthylacetyl-ffgkf, napthylacetyl-FFK(Dmt) (SEQ ID NO: 6), napthylacetyl-FFFK(Dmt) (SEQ ID NO: 7), napthylacetyl-FFGK(Dmt) (SEQ ID NO: 8), napthylacetyl-ffk (dmt), napthylacetyl-fffk(dmt), napthylacetyl-ffgk(dmt), wherein Dmt is 2,6-dimethyl-L-tyrosine and dmt is 2,6-dimethyl-D-tyrosine.

7. The branched peptide according to claim 1, wherein the second peptide chain comprises not more than 50 amino acid residues between the enzyme cleavage site and the covalent bond.

8. The branched peptide according to claim 1, wherein the second peptide chain comprises an enterokinase cleavage site.

9. The branched peptide according to claim 7, wherein the second peptide chain comprises a single amino acid residue between the cleavage site and the covalent bond, where the single amino acid is other than Trp or Pro.

10. The branched peptide according to claim 1, wherein the second peptide chain comprises the amino acid sequence of DDDDK (SEQ ID NO: 17), KDDDK (SEQ ID NO: 18), DDDDR (SEQ ID NO: 19), KDDDR (SEQ ID NO: 20), DYKDDDDK (SEQ ID NO: 35), or DYKDDDDR (SEQ ID NO: 36).

11. The branched peptide according to claim 1, wherein
the second peptide chain comprising the amino acid sequence of SEQ ID NO: 17 is DDDDK(G/A/T/S/Y/H/Q/E/N/D/R/K) (SEQ ID NO: 46), or
the second peptide chain comprising the amino acid sequence of SEQ ID NO: 18 is KDDDK(G/A/T/S/Y/H/Q/E/N/D/R/K) (SEQ ID NO: 47), or
the second peptide chain comprising the amino acid sequence of SEQ ID NO: 19 is DDDDR(G/A/T/S/Y/H/Q/E/N/D/R/K) (SEQ ID NO: 48), or
the second peptide chain comprising the amino acid sequence of SEQ ID NO: 20 is KDDDR(G/A/T/S/Y/H/Q/E/N/D/R/K) (SEQ ID NO: 49), or
the second peptide chain comprising the amino acid sequence of SEQ ID NO: 21 is DADDK(G/A/T/S/Y/H/Q/E/N/D/R/K) (SEQ ID NO: 50), or
the second peptide chain comprising the amino acid sequence of SEQ ID NO: 22 is KADDK(G/A/T/S/Y/H/Q/E/N/D/R/K) (SEQ ID NO: 51), or
the second peptide chain comprising the amino acid sequence of SEQ ID NO: 23 is DADDR(G/A/T/S/Y/H/Q/E/N/D/R/K) (SEQ ID NO: 52), or
the second peptide chain comprising the amino acid sequence of SEQ ID NO: 24 is KADDR(G/A/T/S/Y/H/Q/E/N/D/R/K) (SEQ ID NO: 53), or
the second peptide chain comprising the amino acid sequence of SEQ ID NO: 25 is DEDDK(G/A/T/S/Y/H/Q/E/N/D/R/K) (SEQ ID NO: 54), or
the second peptide chain comprising the amino acid sequence of SEQ ID NO: 26 is KEDDK(G/A/T/S/Y/H/Q/E/N/D/R/K) (SEQ ID NO: 55), or
the second peptide chain comprising the amino acid sequence of SEQ ID NO: 27 is DEDDR(G/A/T/S/Y/H/Q/E/N/D/R/K) (SEQ ID NO: 56), or
the second peptide chain comprising the amino acid sequence of SEQ ID NO: 28 is KEDDR(G/A/T/S/Y/H/Q/E/N/D/R/K) (SEQ ID NO: 57), or
the second peptide chain comprising the amino acid sequence of SEQ ID NO: 29 is EDDDK(G/A/T/S/Y/H/Q/E/N/D/R/K) (SEQ ID NO: 58), or
the second peptide chain comprising the amino acid sequence of SEQ ID NO: 30 is EDDDR(G/A/T/S/Y/H/Q/E/N/D/R/K) (SEQ ID NO: 59), or
the second peptide chain comprising the amino acid sequence of SEQ ID NO: 31 is EEDDK(G/A/T/S/Y/H/Q/E/N/D/R/K) (SEQ ID NO: 60), or
the second peptide chain comprising the amino acid sequence of SEQ ID NO: 32 is EEDDR(G/A/T/S/Y/H/Q/E/N/D/R/K) (SEQ ID NO: 61), or
the second peptide chain comprising the amino acid sequence of SEQ ID NO: 33 is DLYDDDDK(G/A/T/S/Y/H/Q/E/N/D/R/K) (SEQ ID NO: 62), or the second peptide chain comprising the amino acid sequence of SEQ ID NO: 34 is DLYDDDDR(G/A/T/S/Y/H/Q/E/N/D/R/K) (SEQ ID NO: 63), or
the second peptide chain comprising the amino acid sequence of SEQ ID NO: 35 is DYKDDDDK(G/A/T/S/Y/H/Q/E/N/D/R/K) (SEQ ID NO: 64), or
the second peptide chain comprising the amino acid sequence of SEQ ID NO: 36 is DYKDDDDR(G/A/T/S/Y/H/Q/E/N/D/R/K) (SEQ ID NO: 65), or
the second peptide chain comprising the amino acid sequence of SEQ ID NO: 37 is DYKDADDK(G/A/T/S/Y/H/Q/E/N/D/R/K) (SEQ ID NO: 66), or
the second peptide chain comprising the amino acid sequence of SEQ ID NO: 38 is DYKDADDR(G/A/T/S/Y/H/Q/E/N/D/R/K) (SEQ ID NO: 67), or
the second peptide chain comprising the amino acid sequence of SEQ ID NO: 39 is DYKDEDDK(G/A/T/S/Y/H/Q/E/N/D/R/K) (SEQ ID NO: 68), or
the second peptide chain comprising the amino acid sequence of SEQ ID NO: 40 is DYKDEDDR(G/A/T/S/Y/H/Q/E/N/D/R/K) (SEQ ID NO: 69), or
the second peptide chain comprising the amino acid sequence of SEQ ID NO: 41 is DYKEDDDK(G/A/T/S/Y/H/Q/E/N/D/R/K) (SEQ ID NO: 70), or
the second peptide chain comprising the amino acid sequence of SEQ ID NO: 42 is DYKEDDDR(G/A/T/S/Y/H/Q/E/N/D/R/K) (SEQ ID NO: 71), or
the second peptide chain comprising the amino acid sequence of SEQ ID NO: 43 is DYKEEDDK(G/A/T/S/Y/H/Q/E/N/D/R/K) (SEQ ID NO: 72), or
the second peptide chain comprising the amino acid sequence of SEQ ID NO: 44 is DYKEEDDR(G/A/T/S/Y/H/Q/E/N/D/R/K) (SEQ ID NO: 73), or
the second peptide chain comprising the amino acid sequence of SEQ ID NO: 45 is LKGDR(G/A/T/S/Y/H/Q/E/N/D/R/K) (SEQ ID NO: 74).

12. A branched peptide comprising a first peptide chain and a second peptide chain having its C-terminal amino acid covalently linked to a sidechain of a lysine residue of the first peptide chain wherein the branched peptide is selected from the group consisting of:
Nap-FFK($^\varepsilon$G-KDDDDKYD-NH$_2$)Y,
Nap-ffk($^\varepsilon$G-KDDDDKYD-NH$_2$)y,
Nap-FFK($^\varepsilon$G-RDDDDKYD-NH$_2$)Y,
Nap-ffk($^\varepsilon$G-RDDDDKYD-NH$_2$)y,
Nap-FFK($^\varepsilon$G-KDDDDKYD-NH$_2$)(Dmt),
Nap-ffk($^\varepsilon$G-KDDDDKYD-NH$_2$)(dmt),
Nap-FFK($^\varepsilon$G-RDDDDKYD-NH$_2$)(Dmt),
Nap-ffk($^\varepsilon$G-RDDDDKYD-NH$_2$)(dmt),
Nap-FFK($^\varepsilon$G-KDDDDK(DmOD-NH$_2$)Y,
Nap-ffk($^\varepsilon$G-KDDDDK(DmOD-NH$_2$)y,
Nap-FFK($^\varepsilon$G-RDDDDK(DmOD-NH$_2$)Y,
Nap-ffk($^\varepsilon$G-RDDDDK(DmOD-NH$_2$)y,
Nap-FFK($^\varepsilon$G-KDDDDK(DmOD-NH$_2$)(Dmt),
Nap-ffk($^\varepsilon$G-KDDDDK(DmOD-NH$_2$)(dmt),
Nap-FFK($^\varepsilon$G-RDDDDK(DmOD-NH$_2$)(Dmt),
Nap-ffk($^\varepsilon$G-RDDDDK(DmOD-NH$_2$)(dmt),
Nap-FFK($^\varepsilon$G-KDDDDKYD-NH$_2$)Y—Z,
Nap-ffk($^\varepsilon$G-KDDDDKYD-NH$_2$)y-Z,
Nap-FFK($^\varepsilon$G-RDDDDKYD-NH$_2$)Y—Z,
Nap-ffk($^\varepsilon$G-RDDDDKYD-NH$_2$)y-Z,
Nap-FFK($^\varepsilon$G-KDDDDKYD-NH$_2$)(Dmt)-Z,
Nap-ffk($^\varepsilon$G-KDDDDKYD-NH$_2$)(dmt)-Z,
Nap-FFK($^\varepsilon$-RDDDDKYD-NH$_2$)(Dmt)-Z,
Nap-ffk($^\varepsilon$G-RDDDDKYD-NH$_2$)(dmt)-Z,
Nap-FFK($^\varepsilon$G-KDDDDK(DmOD-NH$_2$)Y—Z,
Nap-ffk($^\varepsilon$-KDDDDK(DmOD-NH$_2$)y-Z,
Nap-FFK($^\varepsilon$G-RDDDDK(DmOD-NH$_2$)Y—Z,
Nap-ffk($^\varepsilon$G-RDDDDK(DmOD-NH$_2$)y-Z,
Nap-FFK($^\varepsilon$G-KDDDDK(DmOD-NH$_2$)(Dmt)-Z,
Nap-ffk($^\varepsilon$G-KDDDDK(DmOD-NH$_2$)(dmt)-Z,
Nap-FFK($^\varepsilon$G-RDDDDK(DmOD-NH$_2$)(Dmt)-Z,
Nap-ffk($^\varepsilon$G-RDDDDK(DmOD-NH$_2$)(dmt)-Z,
wherein the lowercase letters denote D-amino acids and the uppercase letters denote L-amino acids,
wherein Nap is

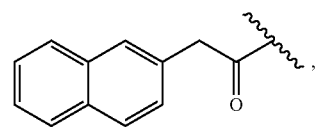

wherein Z is a therapeutic agent covalently bonded to the C-terminal residue of the first peptide chain, and
wherein Dmt is 2,6-dimethyl-L-tyrosine and dmt is 2,6-dimethyl-D-tyrosine.

13. The branched peptide according to claim 1, wherein the first peptide chain further comprises a therapeutic agent, Z, covalently bonded to the C-terminal residue of first peptide chain.

14. The branched peptide according to claim 13, wherein the therapeutic agent, Z, is selected from the group consisting of antioxidants, coenzymes, vitamins, metabolites, analgesics, anti-inflammatory agents, antihelminthics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-thrombogenic agents, anti-claudication agents, anti-atherosclerotic drugs, vascular agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, β-blockers, cardiac inotropic agents, corticosteroids, diuretics, anti-parkinsonian agents, gastro-intestinal agents, histamine receptor antagonists, keratolyptics, lipid regulating agents, anti-anginal agents, Cox-2 inhibitors, leukotriene inhibitors, macrolides, muscle relaxants, nutritional agents, opioid analgesics, protease inhibitors, sex hormones, stimulants, anti-osteoporosis agents, anti-obesity agents, cognition enhancers, anti-urinary incontinence agents, anti-benign prostate hypertrophy agents, essential fatty acids, non-essential fatty acids, cytokines, growth factors, antibodies, radioprotective agents, and cardioprotective agents.

15. A pharmaceutical composition comprising the branched peptide according to claim 1 in an aqueous medium.

16. The pharmaceutical composition according to claim 15, wherein the branched peptides form micelle structures.

17. The pharmaceutical composition according to claim 16 further comprising a therapeutic agent encapsulated within micelle structures.

18. The pharmaceutical composition according to claim 17, wherein the therapeutic agent is selected from the group consisting of analgesics, anti-inflammatory agents, antihelminthics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-thrombogenic agents, anti-claudication agents, anti-atherosclerotic drugs, vascular agents, anti-malarials, anti-migraine agents, anti-muscarinic agents, anti-neoplastic agents (e.g., antiproliferative or chemotherapeutic agents), erectile dysfunction improvement agents, immunosuppressants, anti-protozoal agents, anti-thyroid agents, anxiolytic agents, sedatives, hypnotics, neuroleptics, β-blockers, cardiac inotropic agents, corticosteroids, diuretics, anti-parkinsonian agents, gastro-intestinal agents, histamine receptor antagonists, keratolyptics, lipid regulating agents, anti-anginal agents, Cox-2 inhibitors, leukotriene inhibitors, macrolides, muscle relaxants, nutritional agents, opioid analgesics, protease inhibitors, sex hormones, stimulants, anti-osteoporosis agents, anti-obesity agents, cognition enhancers, anti-urinary incontinence agents, anti-benign prostate hypertrophy agents, essential fatty acids, non-essential fatty acids, antioxidants, and mixtures thereof.

19. A method of delivering a therapeutic agent into mitochondria comprising:
   encapsulating a therapeutic agent within a micelle structure of a pharmaceutical composition according to claim 15; and
   contacting a cell with the pharmaceutical composition, whereby micelle structures are taken up by the cell and targeted to mitochondria within the cell.

* * * * *

SEQUENCE LISTING

```
<160> NUMBER OF SEQ ID NOS: 75

<210> SEQ ID NO 1
<211> LENGTH: 4
<212> TYPE: PRT
<213> ORGANISM: Artificial
<220> FEATURE:
<223> OTHER INFORMATION: Hydrogelator
<220> FEATURE:
<221> NAME/KEY: MISC_FEATURE
<222> LOCATION: (1)..(1)
<223> OTHER INFORMATION: Xaa at position 1 is N-napthylacetyl-
      phenylalanine

<400> SEQUENCE: 1

Xaa Phe Lys Tyr
1

<210> SEQ ID NO 2
<211> LENGTH: 5
<212> TYPE: PRT
<213> ORGANISM: Artificial
<220> FEATURE:
<223> OTHER INFORMATION: Hydrogelator
<220> FEATURE:
<221> NAME/KEY: MISC_FEATURE
<222> LOCATION: (1)..(1)
<223> OTHER INFORMATION: Xaa at position 1 is N-napthylacetyl-
      phenylalanine

<400> SEQUENCE: 2

Xaa Phe Phe Lys Tyr
1               5

<210> SEQ ID NO 3
<211> LENGTH: 5
<212> TYPE: PRT
<213> ORGANISM: Artificial
<220> FEATURE:
<223> OTHER INFORMATION: Hydrogelator
<220> FEATURE:
<221> NAME/KEY: MISC_FEATURE
<222> LOCATION: (1)..(1)
<223> OTHER INFORMATION: Xaa at position 1 is N-napthylacetyl-
      phenylalanine

<400> SEQUENCE: 3
```

```
Xaa Phe Gly Lys Tyr
1               5

<210> SEQ ID NO 4
<211> LENGTH: 4
<212> TYPE: PRT
<213> ORGANISM: Artificial
<220> FEATURE:
<223> OTHER INFORMATION: Hydrogelator
<220> FEATURE:
<221> NAME/KEY: MISC_FEATURE
<222> LOCATION: (1)..(1)
<223> OTHER INFORMATION: Xaa at position 1 is N-napthylacetyl-
      phenylalanine

<400> SEQUENCE: 4

Xaa Phe Gly Lys
1

<210> SEQ ID NO 5
<211> LENGTH: 5
<212> TYPE: PRT
<213> ORGANISM: Artificial
<220> FEATURE:
<223> OTHER INFORMATION: Hydrogelator
<220> FEATURE:
<221> NAME/KEY: MISC_FEATURE
<222> LOCATION: (1)..(1)
<223> OTHER INFORMATION: Xaa at position 1 is N-napthylacetyl-
      phenylalanine

<400> SEQUENCE: 5

Xaa Phe Gly Lys Phe
1               5

<210> SEQ ID NO 6
<211> LENGTH: 4
<212> TYPE: PRT
<213> ORGANISM: Artificial
<220> FEATURE:
<223> OTHER INFORMATION: Hydrogelator
<220> FEATURE:
<221> NAME/KEY: MISC_FEATURE
<222> LOCATION: (1)..(1)
<223> OTHER INFORMATION: Xaa at position 1 is N-napthylacetyl-
      phenylalanine
<220> FEATURE:
<221> NAME/KEY: MISC_FEATURE
<222> LOCATION: (4)..(4)
<223> OTHER INFORMATION: Xaa at position 4 is 2,6-dimethyl-L-tyrosine

<400> SEQUENCE: 6

Xaa Phe Lys Xaa
1

<210> SEQ ID NO 7
<211> LENGTH: 5
<212> TYPE: PRT
<213> ORGANISM: Artificial
<220> FEATURE:
<223> OTHER INFORMATION: Hydrogelator
<220> FEATURE:
<221> NAME/KEY: MISC_FEATURE
<222> LOCATION: (1)..(1)
<223> OTHER INFORMATION: Xaa at position 1 is N-napthylacetyl-
      phenylalanine
<220> FEATURE:
<221> NAME/KEY: MISC_FEATURE
<222> LOCATION: (5)..(5)
<223> OTHER INFORMATION: Xaa at position 5 is 2,6-dimethyl-L-tyrosine
```

-continued

```
<400> SEQUENCE: 7

Xaa Phe Phe Lys Xaa
1               5

<210> SEQ ID NO 8
<211> LENGTH: 5
<212> TYPE: PRT
<213> ORGANISM: Artificial
<220> FEATURE:
<223> OTHER INFORMATION: Hydrogelator
<220> FEATURE:
<221> NAME/KEY: MISC_FEATURE
<222> LOCATION: (1)..(1)
<223> OTHER INFORMATION: Xaa at position 1 is N-napthylacetyl-
      phenylalanine
<220> FEATURE:
<221> NAME/KEY: MISC_FEATURE
<222> LOCATION: (5)..(5)
<223> OTHER INFORMATION: Xaa at position 5 is 2,6-dimethyl-L-tyrosine

<400> SEQUENCE: 8

Xaa Phe Gly Lys Xaa
1               5

<210> SEQ ID NO 9
<211> LENGTH: 4
<212> TYPE: PRT
<213> ORGANISM: Artificial
<220> FEATURE:
<223> OTHER INFORMATION: Hydrogelator
<220> FEATURE:
<221> NAME/KEY: MISC_FEATURE
<222> LOCATION: (1)..(1)
<223> OTHER INFORMATION: Xaa at position 1 is N-napthylacetyl-
      phenylalanine

<400> SEQUENCE: 9

Xaa Phe Cys Tyr
1

<210> SEQ ID NO 10
<211> LENGTH: 5
<212> TYPE: PRT
<213> ORGANISM: Artificial
<220> FEATURE:
<223> OTHER INFORMATION: Hydrogelator
<220> FEATURE:
<221> NAME/KEY: MISC_FEATURE
<222> LOCATION: (1)..(1)
<223> OTHER INFORMATION: Xaa at position 1 is N-napthylacetyl-
      phenylalanine

<400> SEQUENCE: 10

Xaa Phe Phe Cys Tyr
1               5

<210> SEQ ID NO 11
<211> LENGTH: 5
<212> TYPE: PRT
<213> ORGANISM: Artificial
<220> FEATURE:
<223> OTHER INFORMATION: Hydrogelator
<220> FEATURE:
<221> NAME/KEY: MISC_FEATURE
<222> LOCATION: (1)..(1)
<223> OTHER INFORMATION: Xaa at position 1 is N-napthylacetyl-
      phenylalanine

<400> SEQUENCE: 11

Xaa Phe Gly Cys Tyr
```

<210> SEQ ID NO 12
<211> LENGTH: 4
<212> TYPE: PRT
<213> ORGANISM: Artificial
<220> FEATURE:
<223> OTHER INFORMATION: Hydrogelator
<220> FEATURE:
<221> NAME/KEY: MISC_FEATURE
<222> LOCATION: (1)..(1)
<223> OTHER INFORMATION: Xaa at position 1 is N-napthylacetyl-
      phenylalanine

<400> SEQUENCE: 12

Xaa Phe Gly Cys
1

<210> SEQ ID NO 13
<211> LENGTH: 5
<212> TYPE: PRT
<213> ORGANISM: Artificial
<220> FEATURE:
<223> OTHER INFORMATION: Hydrogelator
<220> FEATURE:
<221> NAME/KEY: MISC_FEATURE
<222> LOCATION: (1)..(1)
<223> OTHER INFORMATION: Xaa at position 1 is N-napthylacetyl-
      phenylalanine

<400> SEQUENCE: 13

Xaa Phe Gly Cys Phe
1               5

<210> SEQ ID NO 14
<211> LENGTH: 4
<212> TYPE: PRT
<213> ORGANISM: Artificial
<220> FEATURE:
<223> OTHER INFORMATION: Hydrogelator
<220> FEATURE:
<221> NAME/KEY: MISC_FEATURE
<222> LOCATION: (1)..(1)
<223> OTHER INFORMATION: Xaa at position 1 is N-napthylacetyl-
      phenylalanine
<220> FEATURE:
<221> NAME/KEY: MISC_FEATURE
<222> LOCATION: (4)..(4)
<223> OTHER INFORMATION: Xaa at position at position 4 is 2,6-dimethyl-
      L-tyrosine

<400> SEQUENCE: 14

Xaa Phe Cys Xaa
1

<210> SEQ ID NO 15
<211> LENGTH: 5
<212> TYPE: PRT
<213> ORGANISM: Artificial
<220> FEATURE:
<223> OTHER INFORMATION: Hydrogelator
<220> FEATURE:
<221> NAME/KEY: MISC_FEATURE
<222> LOCATION: (1)..(1)
<223> OTHER INFORMATION: Xaa at position 1 is N-napthylacetyl-
      phenylalanine
<220> FEATURE:
<221> NAME/KEY: MISC_FEATURE
<222> LOCATION: (5)..(5)
<223> OTHER INFORMATION: Xaa at position 5 is 2,6-dimethyl-L-tyrosine

<400> SEQUENCE: 15

Xaa Phe Phe Cys Xaa
1               5

<210> SEQ ID NO 16
<211> LENGTH: 5
<212> TYPE: PRT
<213> ORGANISM: Artificial
<220> FEATURE:
<223> OTHER INFORMATION: Hydrogelator
<220> FEATURE:
<221> NAME/KEY: MISC_FEATURE
<222> LOCATION: (1)..(1)
<223> OTHER INFORMATION: Xaa at position 1 is N-napthylacetyl-
      phenylalanine
<220> FEATURE:
<221> NAME/KEY: MISC_FEATURE
<222> LOCATION: (5)..(5)
<223> OTHER INFORMATION: Xaa at position 5 is 2,6-dimethyl-L-tyrosine

<400> SEQUENCE: 16

Xaa Phe Gly Cys Xaa
1               5

<210> SEQ ID NO 17
<211> LENGTH: 5
<212> TYPE: PRT
<213> ORGANISM: Artificial
<220> FEATURE:
<223> OTHER INFORMATION: Hydrophilic tag

<400> SEQUENCE: 17

Asp Asp Asp Asp Lys
1               5

<210> SEQ ID NO 18
<211> LENGTH: 5
<212> TYPE: PRT
<213> ORGANISM: Artificial
<220> FEATURE:
<223> OTHER INFORMATION: Hydrophilic tag

<400> SEQUENCE: 18

Lys Asp Asp Asp Lys
1               5

<210> SEQ ID NO 19
<211> LENGTH: 5
<212> TYPE: PRT
<213> ORGANISM: Artificial
<220> FEATURE:
<223> OTHER INFORMATION: Hydrophilic tag

<400> SEQUENCE: 19

Asp Asp Asp Asp Arg
1               5

<210> SEQ ID NO 20
<211> LENGTH: 5
<212> TYPE: PRT
<213> ORGANISM: Artificial
<220> FEATURE:
<223> OTHER INFORMATION: Hydrophilic tag

<400> SEQUENCE: 20

Lys Asp Asp Asp Arg
1               5

```
<210> SEQ ID NO 21
<211> LENGTH: 5
<212> TYPE: PRT
<213> ORGANISM: Artificial
<220> FEATURE:
<223> OTHER INFORMATION: Hydrophilic tag

<400> SEQUENCE: 21

Asp Ala Asp Asp Lys
1               5

<210> SEQ ID NO 22
<211> LENGTH: 5
<212> TYPE: PRT
<213> ORGANISM: Artificial
<220> FEATURE:
<223> OTHER INFORMATION: Hydrophilic tag

<400> SEQUENCE: 22

Lys Ala Asp Asp Lys
1               5

<210> SEQ ID NO 23
<211> LENGTH: 5
<212> TYPE: PRT
<213> ORGANISM: Artificial
<220> FEATURE:
<223> OTHER INFORMATION: Hydrophilic tag

<400> SEQUENCE: 23

Asp Ala Asp Asp Arg
1               5

<210> SEQ ID NO 24
<211> LENGTH: 5
<212> TYPE: PRT
<213> ORGANISM: Artificial
<220> FEATURE:
<223> OTHER INFORMATION: Hydrophilic tag

<400> SEQUENCE: 24

Lys Ala Asp Asp Arg
1               5

<210> SEQ ID NO 25
<211> LENGTH: 5
<212> TYPE: PRT
<213> ORGANISM: Artificial
<220> FEATURE:
<223> OTHER INFORMATION: Hydrophilic tag

<400> SEQUENCE: 25

Asp Glu Asp Asp Lys
1               5

<210> SEQ ID NO 26
<211> LENGTH: 5
<212> TYPE: PRT
<213> ORGANISM: Artificial
<220> FEATURE:
<223> OTHER INFORMATION: Hydrophilic tag

<400> SEQUENCE: 26

Lys Glu Asp Asp Lys
1               5

<210> SEQ ID NO 27
```

```
<211> LENGTH: 5
<212> TYPE: PRT
<213> ORGANISM: Artificial
<220> FEATURE:
<223> OTHER INFORMATION: Hydrophilic tag

<400> SEQUENCE: 27

Asp Glu Asp Asp Arg
1               5

<210> SEQ ID NO 28
<211> LENGTH: 5
<212> TYPE: PRT
<213> ORGANISM: Artificial
<220> FEATURE:
<223> OTHER INFORMATION: Hydrophilic tag

<400> SEQUENCE: 28

Lys Glu Asp Asp Arg
1               5

<210> SEQ ID NO 29
<211> LENGTH: 5
<212> TYPE: PRT
<213> ORGANISM: Artificial
<220> FEATURE:
<223> OTHER INFORMATION: Hydrophilic tag

<400> SEQUENCE: 29

Glu Asp Asp Asp Lys
1               5

<210> SEQ ID NO 30
<211> LENGTH: 5
<212> TYPE: PRT
<213> ORGANISM: Artificial
<220> FEATURE:
<223> OTHER INFORMATION: Hydrophilic tag

<400> SEQUENCE: 30

Glu Asp Asp Asp Arg
1               5

<210> SEQ ID NO 31
<211> LENGTH: 5
<212> TYPE: PRT
<213> ORGANISM: Artificial
<220> FEATURE:
<223> OTHER INFORMATION: Hydrophilic tag

<400> SEQUENCE: 31

Glu Glu Asp Asp Lys
1               5

<210> SEQ ID NO 32
<211> LENGTH: 5
<212> TYPE: PRT
<213> ORGANISM: Artificial
<220> FEATURE:
<223> OTHER INFORMATION: Hydrophilic tag

<400> SEQUENCE: 32

Glu Glu Asp Asp Arg
1               5

<210> SEQ ID NO 33
<211> LENGTH: 8
```

```
<212> TYPE: PRT
<213> ORGANISM: Artificial
<220> FEATURE:
<223> OTHER INFORMATION: Hydrophilic tag

<400> SEQUENCE: 33

Asp Leu Tyr Asp Asp Asp Asp Lys
1               5

<210> SEQ ID NO 34
<211> LENGTH: 8
<212> TYPE: PRT
<213> ORGANISM: Artificial
<220> FEATURE:
<223> OTHER INFORMATION: Hydrophilic tag

<400> SEQUENCE: 34

Asp Leu Tyr Asp Asp Asp Asp Arg
1               5

<210> SEQ ID NO 35
<211> LENGTH: 8
<212> TYPE: PRT
<213> ORGANISM: Artificial
<220> FEATURE:
<223> OTHER INFORMATION: Hydrophilic tag

<400> SEQUENCE: 35

Asp Tyr Lys Asp Asp Asp Asp Lys
1               5

<210> SEQ ID NO 36
<211> LENGTH: 8
<212> TYPE: PRT
<213> ORGANISM: Artificial
<220> FEATURE:
<223> OTHER INFORMATION: Hydrophilic tag

<400> SEQUENCE: 36

Asp Tyr Lys Asp Asp Asp Asp Arg
1               5

<210> SEQ ID NO 37
<211> LENGTH: 8
<212> TYPE: PRT
<213> ORGANISM: Artificial
<220> FEATURE:
<223> OTHER INFORMATION: Hydrophilic tag

<400> SEQUENCE: 37

Asp Tyr Lys Asp Ala Asp Asp Lys
1               5

<210> SEQ ID NO 38
<211> LENGTH: 8
<212> TYPE: PRT
<213> ORGANISM: Artificial
<220> FEATURE:
<223> OTHER INFORMATION: Hydrophilic tag

<400> SEQUENCE: 38

Asp Tyr Lys Asp Ala Asp Asp Arg
1               5

<210> SEQ ID NO 39
<211> LENGTH: 8
<212> TYPE: PRT
```

```
<213> ORGANISM: Artificial
<220> FEATURE:
<223> OTHER INFORMATION: Hydrophilic tag

<400> SEQUENCE: 39

Asp Tyr Lys Asp Glu Asp Asp Lys
1               5

<210> SEQ ID NO 40
<211> LENGTH: 8
<212> TYPE: PRT
<213> ORGANISM: Artificial
<220> FEATURE:
<223> OTHER INFORMATION: Hydrophilic tag

<400> SEQUENCE: 40

Asp Tyr Lys Asp Glu Asp Asp Arg
1               5

<210> SEQ ID NO 41
<211> LENGTH: 8
<212> TYPE: PRT
<213> ORGANISM: Artificial
<220> FEATURE:
<223> OTHER INFORMATION: Hydrophilic tag

<400> SEQUENCE: 41

Asp Tyr Lys Glu Asp Asp Asp Lys
1               5

<210> SEQ ID NO 42
<211> LENGTH: 8
<212> TYPE: PRT
<213> ORGANISM: Artificial
<220> FEATURE:
<223> OTHER INFORMATION: Hydrophilic tag

<400> SEQUENCE: 42

Asp Tyr Lys Glu Asp Asp Asp Arg
1               5

<210> SEQ ID NO 43
<211> LENGTH: 8
<212> TYPE: PRT
<213> ORGANISM: Artificial
<220> FEATURE:
<223> OTHER INFORMATION: Hydrophilic tag

<400> SEQUENCE: 43

Asp Tyr Lys Glu Glu Asp Asp Lys
1               5

<210> SEQ ID NO 44
<211> LENGTH: 8
<212> TYPE: PRT
<213> ORGANISM: Artificial
<220> FEATURE:
<223> OTHER INFORMATION: Hydrophilic tag

<400> SEQUENCE: 44

Asp Tyr Lys Glu Glu Asp Asp Arg
1               5

<210> SEQ ID NO 45
<211> LENGTH: 5
<212> TYPE: PRT
<213> ORGANISM: Artificial
```

```
<220> FEATURE:
<223> OTHER INFORMATION: Hydrophilic tag

<400> SEQUENCE: 45

Leu Lys Gly Asp Arg
1               5

<210> SEQ ID NO 46
<211> LENGTH: 6
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
      E, N, D, R, or K

<400> SEQUENCE: 46

Asp Asp Asp Asp Lys Xaa
1               5

<210> SEQ ID NO 47
<211> LENGTH: 6
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
      E, N, D, R, or K

<400> SEQUENCE: 47

Lys Asp Asp Asp Lys Xaa
1               5

<210> SEQ ID NO 48
<211> LENGTH: 6
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
      E, N, D, R, or K

<400> SEQUENCE: 48

Asp Asp Asp Asp Arg Xaa
1               5

<210> SEQ ID NO 49
<211> LENGTH: 6
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
      E, N, D, R, or K

<400> SEQUENCE: 49

Lys Asp Asp Asp Arg Xaa
1               5
```

```
<210> SEQ ID NO 50
<211> LENGTH: 6
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
      E, N, D, R, or K

<400> SEQUENCE: 50

Asp Ala Asp Asp Lys Xaa
1               5

<210> SEQ ID NO 51
<211> LENGTH: 6
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
      E, N, D, R, or K

<400> SEQUENCE: 51

Lys Ala Asp Asp Lys Xaa
1               5

<210> SEQ ID NO 52
<211> LENGTH: 6
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
      E, N, D, R, or K

<400> SEQUENCE: 52

Asp Ala Asp Asp Arg Xaa
1               5

<210> SEQ ID NO 53
<211> LENGTH: 6
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
      E, N, D, R, or K

<400> SEQUENCE: 53

Lys Ala Asp Asp Arg Xaa
1               5

<210> SEQ ID NO 54
<211> LENGTH: 6
<212> TYPE: PRT
<213> ORGANISM: Artificial
<220> FEATURE:
```

<223> OTHER INFORMATION: Hydrophilic tag
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
      E, N, D, R, or K

<400> SEQUENCE: 54

Asp Glu Asp Asp Lys Xaa
1               5

<210> SEQ ID NO 55
<211> LENGTH: 6
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
      E, N, D, R, or K

<400> SEQUENCE: 55

Lys Glu Asp Asp Lys Xaa
1               5

<210> SEQ ID NO 56
<211> LENGTH: 6
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
      E, N, D, R, or K

<400> SEQUENCE: 56

Asp Glu Asp Asp Arg Xaa
1               5

<210> SEQ ID NO 57
<211> LENGTH: 6
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
      E, N, D, R, or K

<400> SEQUENCE: 57

Lys Glu Asp Asp Arg Xaa
1               5

<210> SEQ ID NO 58
<211> LENGTH: 6
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
      E, N, D, R, or K

```
<400> SEQUENCE: 58

Glu Asp Asp Asp Lys Xaa
1               5

<210> SEQ ID NO 59
<211> LENGTH: 6
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
      E, N, D, R, or K

<400> SEQUENCE: 59

Glu Asp Asp Asp Arg Xaa
1               5

<210> SEQ ID NO 60
<211> LENGTH: 6
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
      E, N, D, R, or K

<400> SEQUENCE: 60

Glu Glu Asp Asp Lys Xaa
1               5

<210> SEQ ID NO 61
<211> LENGTH: 6
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
      E, N, D, R, or K

<400> SEQUENCE: 61

Glu Glu Asp Asp Arg Xaa
1               5

<210> SEQ ID NO 62
<211> LENGTH: 9
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (9)..(9)
<223> OTHER INFORMATION: Xaa at position 9 can be G, A, T, S, Y, H, Q,
      E, N, D, R, or K

<400> SEQUENCE: 62

Asp Leu Tyr Asp Asp Asp Asp Lys Xaa
1               5

<210> SEQ ID NO 63
```

```
<211> LENGTH: 9
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (9)..(9)
<223> OTHER INFORMATION: Xaa at position 9 can be G, A, T, S, Y, H, Q,
      E, N, D, R, or K

<400> SEQUENCE: 63

Asp Leu Tyr Asp Asp Asp Asp Arg Xaa
1               5

<210> SEQ ID NO 64
<211> LENGTH: 9
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (9)..(9)
<223> OTHER INFORMATION: Xaa at position 9 can be G, A, T, S, Y, H, Q,
      E, N, D, R, or K

<400> SEQUENCE: 64

Asp Tyr Lys Asp Asp Asp Asp Lys Xaa
1               5

<210> SEQ ID NO 65
<211> LENGTH: 9
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (9)..(9)
<223> OTHER INFORMATION: Xaa at position 9 can be G, A, T, S, Y, H, Q,
      E, N, D, R, or K

<400> SEQUENCE: 65

Asp Tyr Lys Asp Asp Asp Asp Arg Xaa
1               5

<210> SEQ ID NO 66
<211> LENGTH: 9
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (9)..(9)
<223> OTHER INFORMATION: Xaa at position 9 can be G, A, T, S, Y, H, Q,
      E, N, D, R, or K

<400> SEQUENCE: 66

Asp Tyr Lys Asp Ala Asp Asp Lys Xaa
1               5

<210> SEQ ID NO 67
<211> LENGTH: 9
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
```

```
<222> LOCATION: (9)..(9)
<223> OTHER INFORMATION: Xaa at position 9 can be G, A, T, S, Y, H, Q,
      E, N, D, R, or K

<400> SEQUENCE: 67

Asp Tyr Lys Asp Ala Asp Asp Arg Xaa
1               5

<210> SEQ ID NO 68
<211> LENGTH: 9
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (9)..(9)
<223> OTHER INFORMATION: Xaa at position 9 can be G, A, T, S, Y, H, Q,
      E, N, D, R, or K

<400> SEQUENCE: 68

Asp Tyr Lys Asp Glu Asp Asp Lys Xaa
1               5

<210> SEQ ID NO 69
<211> LENGTH: 9
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (9)..(9)
<223> OTHER INFORMATION: Xaa at position 9 can be G, A, T, S, Y, H, Q,
      E, N, D, R, or K

<400> SEQUENCE: 69

Asp Tyr Lys Asp Glu Asp Asp Arg Xaa
1               5

<210> SEQ ID NO 70
<211> LENGTH: 9
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (9)..(9)
<223> OTHER INFORMATION: Xaa at position 9 can be G, A, T, S, Y, H, Q,
      E, N, D, R, or K

<400> SEQUENCE: 70

Asp Tyr Lys Glu Asp Asp Asp Lys Xaa
1               5

<210> SEQ ID NO 71
<211> LENGTH: 9
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (9)..(9)
<223> OTHER INFORMATION: Xaa at position 9 can be G, A, T, S, Y, H, Q,
      E, N, D, R, or K

<400> SEQUENCE: 71

Asp Tyr Lys Glu Asp Asp Asp Arg Xaa
```

```
<210> SEQ ID NO 72
<211> LENGTH: 9
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (9)..(9)
<223> OTHER INFORMATION: Xaa at position 9 can be G, A, T, S, Y, H, Q,
      E, N, D, R, or K

<400> SEQUENCE: 72

Asp Tyr Lys Glu Glu Asp Asp Lys Xaa
1               5

<210> SEQ ID NO 73
<211> LENGTH: 9
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (9)..(9)
<223> OTHER INFORMATION: Xaa at position 9 can be G, A, T, S, Y, H, Q,
      E, N, D, R, or K

<400> SEQUENCE: 73

Asp Tyr Lys Glu Glu Asp Asp Arg Xaa
1               5

<210> SEQ ID NO 74
<211> LENGTH: 6
<212> TYPE: PRT
<213> ORGANISM: Artificial
<220> FEATURE:
<223> OTHER INFORMATION: Hydrophilic tag
<220> FEATURE:
<221> NAME/KEY: MISC_FEATURE
<222> LOCATION: (6)..(6)
<223> OTHER INFORMATION: Xaa at position 6 can be G, A, T, S, Y, H, Q,
      E, N, D, R, or K

<400> SEQUENCE: 74

Leu Lys Gly Asp Arg Xaa
1               5

<210> SEQ ID NO 75
<211> LENGTH: 9
<212> TYPE: PRT
<213> ORGANISM: Artificial
<220> FEATURE:
<223> OTHER INFORMATION: Hydrophilic tag

<400> SEQUENCE: 75

Asp Tyr Lys Asp Asp Asp Asp Lys Gly
1               5
```